United States Patent
Hwang et al.

(10) Patent No.: US 9,211,362 B2
(45) Date of Patent: Dec. 15, 2015

(54) SCAFFOLD FOR CONNECTIVE TISSUE REPAIR

(75) Inventors: Julia Hwang, Wayland, MA (US);
Joseph Hammer, Bridgewater, NJ (US);
Herb Schwartz, Fort Wayne, IN (US);
Prasanna Malaviya, Fort Wayne, IN (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

(21) Appl. No.: 13/491,985

(22) Filed: Jun. 8, 2012

(65) Prior Publication Data

US 2012/0253464 A1    Oct. 4, 2012

Related U.S. Application Data

(62) Division of application No. 10/610,362, filed on Jun. 30, 2003, now Pat. No. 8,226,715.

(51) Int. Cl.
*A61F 2/08* (2006.01)
*A61L 27/36* (2006.01)
(Continued)

(52) U.S. Cl.
CPC ............ *A61L 27/3604* (2013.01); *A61F 2/08* (2013.01); *A61L 27/18* (2013.01); *A61L 27/3641* (2013.01);
(Continued)

(58) Field of Classification Search
CPC ............ A61F 2002/0852; A61F 2002/30006; A61F 2002/30008; A61F 2002/30009; A61F 2/08; A61F 2/0811; A61F 13/065; A61F 2250/0015; A61F 2250/0028; A61F 2/0063; A61F 2250/0017; A61F 2250/0023; A61F 2002/0068; A61F 2002/30062; A61F 2002/30576; A61F 2002/30578; A61L 27/386; A61L 27/3662; A61L 27/3604; A61L 27/3629; A61L 27/286
USPC ............... 623/13.11–13.2, 23.75; 606/154
See application file for complete search history.

(56) References Cited

U.S. PATENT DOCUMENTS

| | | |
|---|---|---|
| 3,272,204 A | 9/1966 | Artandi |
| 3,562,820 A | 2/1971 | Bernhard |

(Continued)

FOREIGN PATENT DOCUMENTS

| | | |
|---|---|---|
| AU | 717552 B2 | 3/2000 |
| CA | 2247158 A1 | 8/1997 |

(Continued)

OTHER PUBLICATIONS

Sampath, T. K., et al. "In Vitro Transformation of Mesenchymal Cells Derived From Embryonic Muscle Into Cartilage in Response to Extracellular Matrix Components of Bone," Proceedings of the National Academy of Science of the USA, 81(1): 3419-3423 (Jun. 1984).

(Continued)

*Primary Examiner* — Thomas J Sweet
*Assistant Examiner* — Cheryl Miller

(57) ABSTRACT

A connective tissue scaffold including opposed first and second anchoring segments formed from a plurality of bioresorbable polymeric fibers oriented in a direction substantially parallel to a longitudinal axis of the scaffold and a plurality of bioresorbable polymeric fibers oriented in a direction substantially transverse to a longitudinal axis of the scaffold. A central segment joins the first and second anchoring segments and includes a plurality of bioresorbable polymeric fibers oriented in a direction substantially parallel to the longitudinal axis of the scaffold. The scaffold can also a tissue particle and/or biological component.

19 Claims, 5 Drawing Sheets

(51) Int. Cl.
*A61L 27/18* (2006.01)
*A61L 27/56* (2006.01)
*A61L 27/58* (2006.01)

(52) U.S. Cl.
CPC ............ *A61L 27/3645* (2013.01); *A61L 27/56* (2013.01); *A61F 2002/0852* (2013.01); *A61F 2210/0004* (2013.01); *A61F 2250/0015* (2013.01); *A61F 2250/0028* (2013.01); *A61L 27/3662* (2013.01); *A61L 27/3691* (2013.01); *A61L 27/58* (2013.01)

(56) References Cited

U.S. PATENT DOCUMENTS

| | | | |
|---|---|---|---|
| 3,739,402 | A | 6/1973 | Cooley et al. |
| 3,812,017 | A | 5/1974 | Santangelo et al. |
| 3,857,932 | A | 12/1974 | Shepherd et al. |
| 4,045,418 | A | 8/1977 | Sinclair |
| 4,057,537 | A | 11/1977 | Sinclair |
| 4,105,034 | A | 8/1978 | Shalaby et al. |
| 4,130,639 | A | 12/1978 | Shalaby et al. |
| 4,130,689 | A | 12/1978 | Costa, Jr. |
| 4,140,678 | A | 2/1979 | Shalaby et al. |
| 4,141,087 | A | 2/1979 | Shalaby et al. |
| 4,205,399 | A | 6/1980 | Shalaby et al. |
| 4,208,511 | A | 6/1980 | Shalaby et al. |
| 4,344,193 | A | 8/1982 | Kenny |
| 4,520,821 | A | 6/1985 | Schmidt et al. |
| 4,553,272 | A | 11/1985 | Mears |
| 4,597,766 | A | 7/1986 | Hilal et al. |
| 4,609,551 | A | 9/1986 | Caplan et al. |
| 4,728,329 | A | 3/1988 | Mansat |
| 4,801,299 | A | 1/1989 | Brendel et al. |
| 4,837,285 | A | 6/1989 | Berg et al. |
| 4,902,508 | A | 2/1990 | Badylak et al. |
| 4,917,700 | A | 4/1990 | Aikins |
| 4,946,377 | A * | 8/1990 | Kovach .................... 623/13.18 |
| 5,007,934 | A | 4/1991 | Stone |
| 5,041,138 | A | 8/1991 | Vacanti et al. |
| 5,053,050 | A | 10/1991 | Itay |
| 5,061,281 | A | 10/1991 | Mares et al. |
| 5,078,744 | A | 1/1992 | Chvapil |
| 5,108,807 | A | 4/1992 | Tucker |
| 5,108,989 | A | 4/1992 | Amento et al. |
| 5,147,400 | A | 9/1992 | Kaplan et al. |
| 5,176,708 | A | 1/1993 | Frey et al. |
| 5,206,023 | A | 4/1993 | Hunziker et al. |
| 5,258,028 | A | 11/1993 | Ersek et al. |
| 5,263,984 | A * | 11/1993 | Li et al. .................... 623/13.18 |
| 5,290,494 | A | 3/1994 | Coombes et al. |
| 5,306,311 | A | 4/1994 | Stone et al. |
| 5,320,624 | A | 6/1994 | Kaplan et al. |
| 5,320,646 | A | 6/1994 | Patton et al. |
| 5,326,357 | A | 7/1994 | Kandel et al. |
| 5,366,756 | A | 11/1994 | Chesterfield et al. |
| 5,393,594 | A * | 2/1995 | Koyfman et al. ............ 442/414 |
| 5,425,766 | A | 6/1995 | Bowald et al. |
| 5,443,950 | A | 8/1995 | Naughton et al. |
| 5,445,833 | A | 8/1995 | Badylak et al. |
| 5,455,041 | A | 10/1995 | Genco et al. |
| 5,464,929 | A | 11/1995 | Bezwada et al. |
| 5,468,253 | A | 11/1995 | Bezwada et al. |
| 5,480,827 | A | 1/1996 | Guillemin et al. |
| 5,487,897 | A | 1/1996 | Polson et al. |
| 5,514,181 | A | 5/1996 | Light et al. |
| 5,514,378 | A | 5/1996 | Mikos et al. |
| 5,571,189 | A | 11/1996 | Kuslich |
| 5,577,517 | A | 11/1996 | Bonutti |
| 5,589,176 | A | 12/1996 | Seare, Jr. |
| 5,595,751 | A | 1/1997 | Bezwada et al. |
| 5,597,579 | A | 1/1997 | Bezwada et al. |
| 5,607,687 | A | 3/1997 | Bezwada et al. |
| 5,612,028 | A | 3/1997 | Sackier et al. |
| 5,618,552 | A | 4/1997 | Bezwada et al. |
| 5,620,698 | A | 4/1997 | Bezwada et al. |
| 5,624,463 | A | 4/1997 | Stone et al. |
| 5,626,611 | A | 5/1997 | Liu et al. |
| 5,632,745 | A | 5/1997 | Schwartz |
| 5,645,850 | A | 7/1997 | Bezwada et al. |
| 5,648,088 | A | 7/1997 | Bezwada et al. |
| 5,654,135 | A | 8/1997 | Tinois et al. |
| 5,656,492 | A | 8/1997 | Glowacki et al. |
| 5,677,355 | A | 10/1997 | Shalaby et al. |
| 5,681,353 | A | 10/1997 | Li et al. |
| 5,697,976 | A | 12/1997 | Chesterfield et al. |
| 5,698,213 | A | 12/1997 | Jamiolkowski et al. |
| 5,700,583 | A | 12/1997 | Jamiolkowski et al. |
| 5,705,181 | A * | 1/1998 | Cooper et al. ............ 424/426 |
| 5,709,854 | A | 1/1998 | Griffith-Cima et al. |
| 5,713,920 | A | 2/1998 | Bezwada et al. |
| 5,720,969 | A | 2/1998 | Gentile et al. |
| 5,723,331 | A | 3/1998 | Tubo et al. |
| 5,735,903 | A | 4/1998 | Li et al. |
| 5,736,372 | A | 4/1998 | Vacanti et al. |
| 5,755,791 | A | 5/1998 | Whitson et al. |
| 5,759,190 | A | 6/1998 | Vibe-Hansen et al. |
| 5,766,631 | A | 6/1998 | Arnold et al. |
| 5,769,899 | A | 6/1998 | Schwartz et al. |
| 5,782,914 | A | 7/1998 | Schankereli |
| 5,786,217 | A | 7/1998 | Tubo et al. |
| 5,800,537 | A | 9/1998 | Bell |
| 5,800,543 | A * | 9/1998 | McLeod et al. ............ 623/13.2 |
| 5,830,493 | A | 11/1998 | Yokota et al. |
| 5,837,235 | A | 11/1998 | Mueller et al. |
| 5,837,278 | A | 11/1998 | Geistlich et al. |
| 5,842,477 | A | 12/1998 | Naughton et al. |
| 5,855,608 | A | 1/1999 | Brekke et al. |
| 5,859,150 | A | 1/1999 | Jamiolkowski et al. |
| 5,891,558 | A | 4/1999 | Bell et al. |
| 5,902,741 | A | 5/1999 | Purchio et al. |
| 5,904,716 | A | 5/1999 | Gendler |
| 5,904,717 | A | 5/1999 | Brekke et al. |
| 5,914,121 | A | 6/1999 | Robey et al. |
| 5,922,025 | A | 7/1999 | Hubbard |
| 5,964,805 | A | 10/1999 | Stone |
| 5,968,096 | A | 10/1999 | Whitson et al. |
| 5,980,889 | A | 11/1999 | Butler et al. |
| 5,989,269 | A | 11/1999 | Vibe-Hansen et al. |
| 5,990,194 | A | 11/1999 | Dunn et al. |
| 5,990,378 | A | 11/1999 | Ellis et al. |
| 6,001,352 | A | 12/1999 | Boyan et al. |
| 6,001,394 | A | 12/1999 | Daculsi et al. |
| 6,005,161 | A | 12/1999 | Brekke et al. |
| 6,027,742 | A | 2/2000 | Lee et al. |
| 6,042,534 | A * | 3/2000 | Gellman et al. ............ 600/30 |
| 6,042,610 | A | 3/2000 | Li et al. |
| 6,054,122 | A | 4/2000 | MacPhee et al. |
| 6,077,989 | A | 6/2000 | Kandel et al. |
| 6,080,579 | A | 6/2000 | Hanley, Jr. et al. |
| 6,096,532 | A | 8/2000 | Armstrong et al. |
| 6,103,255 | A | 8/2000 | Levene et al. |
| 6,110,209 | A | 8/2000 | Stone |
| 6,110,212 | A | 8/2000 | Gregory |
| 6,113,640 | A * | 9/2000 | Tormala et al. ............ 623/18.11 |
| 6,117,166 | A | 9/2000 | Winston et al. |
| 6,120,514 | A | 9/2000 | Vibe-Hansen et al. |
| 6,121,042 | A | 9/2000 | Peterson et al. |
| 6,123,727 | A | 9/2000 | Vacanti et al. |
| 6,132,463 | A | 10/2000 | Lee et al. |
| 6,132,468 | A | 10/2000 | Mansmann |
| 6,139,578 | A | 10/2000 | Lee et al. |
| 6,140,039 | A | 10/2000 | Naughton et al. |
| 6,143,293 | A | 11/2000 | Weiss et al. |
| 6,147,135 | A | 11/2000 | Yuan et al. |
| 6,153,292 | A | 11/2000 | Bell et al. |
| 6,156,068 | A | 12/2000 | Walter et al. |
| 6,165,217 | A | 12/2000 | Hayes |
| 6,171,338 | B1 | 1/2001 | Talja et al. |
| 6,176,880 | B1 | 1/2001 | Plouhar et al. |
| 6,179,840 | B1 | 1/2001 | Bowman |
| 6,179,872 | B1 | 1/2001 | Bell et al. |
| 6,180,007 | B1 | 1/2001 | Gentile et al. |
| 6,183,737 | B1 | 2/2001 | Zaleske et al. |

(56) References Cited

U.S. PATENT DOCUMENTS

| | | | |
|---|---|---|---|
| 6,187,053 B1 | 2/2001 | Minuth et al. |
| 6,187,329 B1 | 2/2001 | Agrawal et al. |
| 6,197,061 B1 | 3/2001 | Masuda et al. |
| 6,197,325 B1 | 3/2001 | MacPhee et al. |
| 6,200,606 B1 | 3/2001 | Peterson et al. |
| 6,214,045 B1 | 4/2001 | Corbitt, Jr. et al. |
| 6,214,055 B1 | 4/2001 | Simionescu et al. |
| 6,242,247 B1 | 6/2001 | Rieser et al. |
| 6,251,673 B1 | 6/2001 | Winkler et al. |
| 6,277,151 B1 | 8/2001 | Lee et al. |
| 6,283,980 B1 | 9/2001 | Vibe-Hansen et al. |
| 6,287,316 B1 | 9/2001 | Agarwal et al. |
| 6,287,340 B1 | 9/2001 | Altman et al. |
| 6,291,240 B1 | 9/2001 | Mansbridge et al. |
| 6,306,177 B1 | 10/2001 | Felt et al. |
| 6,306,424 B1 | 10/2001 | Vyakarnam et al. |
| 6,316,692 B1 | 11/2001 | Readhead et al. |
| 6,319,712 B1 | 11/2001 | Meenen et al. |
| 6,328,765 B1 * | 12/2001 | Hardwick et al. ......... 623/23.72 |
| 6,331,312 B1 | 12/2001 | Lee et al. |
| 6,333,029 B1 | 12/2001 | Vyakarnam et al. |
| 6,365,149 B2 | 4/2002 | Vyakarnam et al. |
| 6,378,527 B1 | 4/2002 | Hungerford et al. |
| 6,378,572 B1 | 4/2002 | Neubauer et al. |
| 6,379,367 B1 | 4/2002 | Vibe-Hansen et al. |
| 6,464,729 B1 | 10/2002 | Kandel |
| 6,485,723 B1 | 11/2002 | Badylak et al. |
| 6,489,165 B2 | 12/2002 | Bhatnagar et al. |
| 6,503,278 B1 | 1/2003 | Pohjonen et al. |
| 6,511,511 B1 | 1/2003 | Slivka et al. |
| 6,511,958 B1 | 1/2003 | Atkinson et al. |
| 6,521,430 B1 | 2/2003 | Orwar et al. |
| 6,530,956 B1 | 3/2003 | Mansmann |
| 6,534,084 B1 | 3/2003 | Vyakarnam et al. |
| 6,541,024 B1 | 4/2003 | Kadiyala et al. |
| 6,551,355 B1 | 4/2003 | Lewandrowski et al. |
| 6,569,172 B2 | 5/2003 | Asculai et al. |
| 6,592,588 B1 | 7/2003 | Bobic et al. |
| 6,599,323 B2 | 7/2003 | Melican et al. |
| 6,605,294 B2 | 8/2003 | Sawhney |
| 6,626,950 B2 | 9/2003 | Brown et al. |
| 6,652,450 B2 * | 11/2003 | Neisz et al. ......... 600/30 |
| 6,652,585 B2 * | 11/2003 | Lange ......... 623/17.11 |
| 6,727,224 B1 | 4/2004 | Zhang et al. |
| 6,773,458 B1 | 8/2004 | Brauker et al. |
| 6,783,712 B2 | 8/2004 | Slivka et al. |
| 6,840,962 B1 | 1/2005 | Vacanti et al. |
| 6,852,330 B2 | 2/2005 | Bowman et al. |
| 6,866,681 B2 | 3/2005 | Laboureau et al. |
| 6,884,428 B2 | 4/2005 | Binette et al. |
| 6,886,568 B2 | 5/2005 | Frondoza et al. |
| 6,886,569 B2 | 5/2005 | Chervitz et al. |
| 6,902,932 B2 * | 6/2005 | Altman et al. ......... 435/395 |
| 6,946,003 B1 * | 9/2005 | Wolowacz et al. ......... 623/23.72 |
| 7,109,034 B2 | 9/2006 | Orwar et al. |
| 7,208,177 B2 | 4/2007 | Geistlich et al. |
| 7,262,020 B2 | 8/2007 | Hellerstein |
| 7,316,822 B2 | 1/2008 | Binette et al. |
| 7,368,124 B2 | 5/2008 | Chun et al. |
| 7,456,012 B2 | 11/2008 | Ryttsen et al. |
| 7,799,089 B2 | 9/2010 | Plouhar et al. |
| 7,824,701 B2 | 11/2010 | Binette et al. |
| 7,875,296 B2 | 1/2011 | Binette et al. |
| 7,901,461 B2 | 3/2011 | Harmon et al. |
| 8,137,686 B2 | 3/2012 | Kladakis et al. |
| 8,137,702 B2 | 3/2012 | Binette et al. |
| 8,197,837 B2 | 6/2012 | Jamiolkowski et al. |
| 8,221,780 B2 | 7/2012 | Dhanaraj et al. |
| 8,226,715 B2 * | 7/2012 | Hwang et al. ......... 623/13.14 |
| 8,496,970 B2 | 7/2013 | Binette et al. |
| 8,637,066 B2 | 1/2014 | Binnette et al. |
| 8,641,775 B2 | 2/2014 | Harmon et al. |
| 2001/0014475 A1 | 8/2001 | Frondoza et al. |
| 2001/0016353 A1 | 8/2001 | Janas et al. |
| 2001/0016772 A1 | 8/2001 | Lee et al. |
| 2001/0023373 A1 | 9/2001 | Plouhar et al. |
| 2001/0033857 A1 | 10/2001 | Vyakarnam et al. |
| 2001/0038848 A1 | 11/2001 | Donda et al. |
| 2001/0039453 A1 | 11/2001 | Gresser et al. |
| 2001/0051834 A1 | 12/2001 | Frondoza et al. |
| 2001/0053353 A1 | 12/2001 | Griffith et al. |
| 2001/0053839 A1 | 12/2001 | Noishiki et al. |
| 2002/0006428 A1 | 1/2002 | Mahmood et al. |
| 2002/0009477 A1 | 1/2002 | Mahmood et al. |
| 2002/0009805 A1 | 1/2002 | Nevo et al. |
| 2002/0009806 A1 | 1/2002 | Hicks, Jr. |
| 2002/0013627 A1 | 1/2002 | Geistlich et al. |
| 2002/0015719 A1 | 2/2002 | Kellner et al. |
| 2002/0022883 A1 | 2/2002 | Burg |
| 2002/0022884 A1 | 2/2002 | Mansmann |
| 2002/0028192 A1 | 3/2002 | Dimitrijevich et al. |
| 2002/0029055 A1 | 3/2002 | Bonutti |
| 2002/0038151 A1 * | 3/2002 | Plouhar et al. ............. 623/23.72 |
| 2002/0062151 A1 | 5/2002 | Altman et al. |
| 2002/0082631 A1 | 6/2002 | Bonutti |
| 2002/0083479 A1 | 6/2002 | Winston et al. |
| 2002/0091403 A1 | 7/2002 | Bonutti |
| 2002/0091406 A1 | 7/2002 | Bonutti |
| 2002/0099401 A1 | 7/2002 | Bonutti |
| 2002/0099448 A1 | 7/2002 | Hiles et al. |
| 2002/0107570 A1 | 8/2002 | Sybert et al. |
| 2002/0119177 A1 | 8/2002 | Bowman et al. |
| 2002/0120348 A1 | 8/2002 | Melican et al. |
| 2002/0123750 A1 | 9/2002 | Eisermann et al. |
| 2002/0127265 A1 | 9/2002 | Bowman et al. |
| 2002/0133229 A1 | 9/2002 | Laurencin et al. |
| 2002/0133235 A1 | 9/2002 | Hungerford et al. |
| 2002/0150604 A1 | 10/2002 | Yi et al. |
| 2002/0151975 A1 | 10/2002 | Farr et al. |
| 2002/0173558 A1 | 11/2002 | Williams et al. |
| 2002/0176893 A1 | 11/2002 | Wironen et al. |
| 2002/0177224 A1 | 11/2002 | Madry et al. |
| 2003/0003153 A1 | 1/2003 | Asculai et al. |
| 2003/0004578 A1 | 1/2003 | Brown et al. |
| 2003/0012805 A1 | 1/2003 | Chen et al. |
| 2003/0023316 A1 * | 1/2003 | Brown et al. ............. 623/23.72 |
| 2003/0026787 A1 | 2/2003 | Fearnot et al. |
| 2003/0027332 A1 | 2/2003 | Lafrance et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0045937 A1 * | 3/2003 | Ginn ......... 623/17.11 |
| 2003/0050709 A1 | 3/2003 | Noth et al. |
| 2003/0064917 A1 | 4/2003 | Crawford et al. |
| 2003/0075822 A1 | 4/2003 | Slivka et al. |
| 2003/0077311 A1 | 4/2003 | Vyakarnam et al. |
| 2003/0078617 A1 | 4/2003 | Schwartz et al. |
| 2003/0147935 A1 | 8/2003 | Binette et al. |
| 2003/0193104 A1 | 10/2003 | Melican et al. |
| 2004/0024457 A1 * | 2/2004 | Boyce et al. ............. 623/13.17 |
| 2004/0059416 A1 | 3/2004 | Murray et al. |
| 2004/0078077 A1 | 4/2004 | Binette et al. |
| 2004/0078090 A1 | 4/2004 | Binette et al. |
| 2004/0175408 A1 | 9/2004 | Chun et al. |
| 2004/0219182 A1 | 11/2004 | Gomes et al. |
| 2004/0236424 A1 | 11/2004 | Berez et al. |
| 2004/0249457 A1 * | 12/2004 | Smith et al. ......... 623/7 |
| 2004/0267088 A1 * | 12/2004 | Kammerer ......... 600/37 |
| 2004/0267362 A1 | 12/2004 | Hwang et al. |
| 2005/0002915 A1 | 1/2005 | Atala et al. |
| 2005/0038520 A1 | 2/2005 | Binette et al. |
| 2005/0048651 A1 | 3/2005 | Ryttsen et al. |
| 2005/0113937 A1 | 5/2005 | Binette et al. |
| 2005/0113938 A1 | 5/2005 | Jamiolkowski et al. |
| 2005/0125077 A1 | 6/2005 | Harmon et al. |
| 2005/0147645 A1 | 7/2005 | Budny |
| 2005/0177249 A1 | 8/2005 | Kladakis et al. |
| 2005/0232967 A1 | 10/2005 | Kladakis et al. |
| 2005/0234549 A1 | 10/2005 | Kladakis et al. |
| 2006/0067967 A1 | 3/2006 | Bowman et al. |
| 2006/0084930 A1 | 4/2006 | Dhanaraj et al. |
| 2006/0204439 A1 | 9/2006 | Hellerstein |
| 2006/0223177 A1 | 10/2006 | Harris et al. |

(56) References Cited

U.S. PATENT DOCUMENTS

| | | |
|---|---|---|
| 2006/0280768 A1 | 12/2006 | Hwang et al. |
| 2006/0293760 A1 | 12/2006 | DeDeyne |
| 2007/0031470 A1 | 2/2007 | Kladakis et al. |
| 2007/0036767 A1 | 2/2007 | Mistry et al. |
| 2007/0250177 A1 | 10/2007 | Bilbo |
| 2008/0039955 A1 | 2/2008 | Hunziker |
| 2008/0071385 A1 | 3/2008 | Binette et al. |
| 2008/0226870 A1 | 9/2008 | Sypeck et al. |
| 2008/0241213 A1 | 10/2008 | Chun et al. |
| 2011/0009963 A1 | 1/2011 | Binnette et al. |
| 2011/0091517 A1 | 4/2011 | Binette et al. |
| 2011/0097381 A1 | 4/2011 | Binette et al. |
| 2011/0110958 A1 | 5/2011 | Qiu et al. |
| 2011/0177134 A1 | 7/2011 | Harmon et al. |
| 2012/0156265 A1 | 6/2012 | Binette et al. |
| 2012/0165939 A1 | 6/2012 | Kladakis et al. |
| 2013/0123937 A1 | 5/2013 | Jamiolkowski et al. |

FOREIGN PATENT DOCUMENTS

| | | |
|---|---|---|
| DE | 19812195 A1 | 9/1999 |
| EP | 0145492 A2 | 6/1985 |
| EP | 0274898 A2 | 7/1988 |
| EP | 0277678 A1 | 8/1988 |
| EP | 0 411 545 A1 | 2/1991 |
| EP | 0 466 105 A2 | 1/1992 |
| EP | 0464163 A1 | 1/1992 |
| EP | 0 485 215 A1 | 5/1992 |
| EP | 0 562 864 | 9/1993 |
| EP | 0 955 024 | 11/1999 |
| EP | 1027897 A1 | 8/2000 |
| EP | 1 064 958 | 1/2001 |
| EP | 1 074 270 A1 | 2/2001 |
| EP | 1 167 517 | 1/2002 |
| EP | 1177800 A1 | 2/2002 |
| EP | 1 216 717 A1 | 6/2002 |
| EP | 1 216 718 A | 6/2002 |
| EP | 1348451 A1 | 10/2003 |
| EP | 1405649 A1 | 4/2004 |
| EP | 1410811 A1 | 4/2004 |
| EP | 1506790 A1 | 2/2005 |
| EP | 1537839 A1 | 6/2005 |
| EP | 1604622 A1 | 12/2005 |
| FR | 2688690 A1 | 9/1993 |
| GB | 1008193 A | 10/1965 |
| JP | 02-052648 A | 2/1990 |
| JP | 2143945 A | 6/1990 |
| JP | 02-227442 A | 9/1990 |
| JP | 02-256824 A | 10/1990 |
| JP | 03-261753 A | 11/1991 |
| JP | 04-094329 A | 3/1992 |
| JP | H04-502715 A | 5/1992 |
| JP | 10-129048 A | 5/1998 |
| JP | 10234844 A | 9/1998 |
| JP | 10-319783 A | 12/1998 |
| JP | 11-319068 A | 11/1999 |
| JP | H11-512626 A | 11/1999 |
| JP | 3-139361 B2 | 2/2001 |
| JP | 2001-079079 A | 3/2001 |
| JP | 2001129073 A | 5/2001 |
| JP | 2002-165345 A | 6/2002 |
| JP | 2002-527402 A | 8/2002 |
| JP | 2002-272833 A | 9/2002 |
| JP | 2002-535378 A | 10/2002 |
| JP | 2003320008 A | 11/2003 |
| JP | 2004008437 A | 1/2004 |
| JP | 2004-195103 A | 7/2004 |
| JP | 2005-237476 A | 9/2005 |
| JP | 4-300557 B2 | 7/2009 |
| RU | 2187261 C1 | 8/2002 |
| SU | 1535542 A1 | 1/1990 |
| WO | 86/00533 | 1/1986 |
| WO | 9206179 A1 | 4/1992 |
| WO | 93/02718 A1 | 2/1993 |
| WO | 93/11805 A1 | 6/1993 |
| WO | 95/33821 | 12/1995 |
| WO | 96/08277 A1 | 3/1996 |
| WO | 97/30662 | 8/1997 |
| WO | 97/46665 | 12/1997 |
| WO | 98/48860 | 11/1998 |
| WO | 9853768 A1 | 12/1998 |
| WO | 9905992 A1 | 2/1999 |
| WO | 99/16381 | 4/1999 |
| WO | 9939724 A1 | 8/1999 |
| WO | 99/47097 | 9/1999 |
| WO | 9959647 A1 | 11/1999 |
| WO | 00/15248 A2 | 3/2000 |
| WO | 00/16381 A1 | 3/2000 |
| WO | 00/69355 A1 | 11/2000 |
| WO | 00/72782 A1 | 12/2000 |
| WO | 00/74741 A2 | 12/2000 |
| WO | 01/15753 A1 | 3/2001 |
| WO | 01/34065 A1 | 5/2001 |
| WO | 01/85226 A1 | 11/2001 |
| WO | 02/00272 A2 | 1/2002 |
| WO | 02/05750 A2 | 1/2002 |
| WO | 02/30324 A1 | 4/2002 |
| WO | 02062357 A1 | 8/2002 |
| WO | 02/074356 A1 | 9/2002 |
| WO | 02/096268 A2 | 12/2002 |
| WO | 03/007789 A2 | 1/2003 |
| WO | 03/017826 A2 | 3/2003 |
| WO | 03043674 A1 | 5/2003 |
| WO | 2004012782 A1 | 2/2004 |

OTHER PUBLICATIONS

Schreiber RE., et al. "A Method for Tissue Engineering of cartilage by Cell Seeding on Bioresorbable Scaffolds," Ann NY Acad Sci. 875:394-404 (1999) (Abstract Only).

Solov'ev et al., "Functional Activity of Hepatocytes in Liver Fragments In Vitro as a Function if Fragment Size and Duration of Culturing" Bull Exp Biol Med. Jun. 2000;129(6):595-7.

Spaans et al. "Solvent-free fabrication of micro-porous polyurethane amide and polyurethane-urea scaffolds for repair and replacement of the knee joint meniscus" Journal of Biomaterials, vol. 21, No. 23, 2000, pp. 2453-2460.

Stone, K. et al. "Meniscal Regeneration with Copolymeric Collagen Scaffolds," American Journal of Sports Medicine 20(2):104-111 (1992).

Takeuchi et al., The present situation and vision of joint transplantation. Journal of Clinical and Experimental Medicine. 1995;164(10):748-9. Translation.

Tienen T. G. et al., "A porous polymer scaffold for meniscal lesion repair—A study in dogs" Biomaterials, vol. 24, No. 14, 2003, pp. 2541-2548.

Tozum et al., J Canadian Dental Assoc. Nov. 2003 69(10):664-664h.

Trenite, M.D., G.J. Nolst et al.., "Reimplantation of autologous septal cartilage in the growing nasal septum", Rhinology, 25, 1987, pp. 225-236.

van Susante JLC, et al. "Linkage of Chondroitin-Sulfate to Type I Collagen Scaffolds Stimulates the Bioactivity of Seeded Chondrocytes in Vitro", Biomaterials 22(17):2359-2369 (2001) (Abstract Only).

Vandorpe, et al in the Handbook of Biodegradable Polymers, edited by Domb, et al., Hardwood Academic Press, pp. 161-182 (1997).

Young, A.T., Microcellular Foams via Phase Separation, J. Vac. Sci. Technolol., vol. 4(3), May/Jun. 1986.

[No Author] www.bio-medicine.org/medicine-technology-1/New-Study-Shows-Cloning-From-Dried-Cells-Now-Possible-2988-1/, 2 pgs, printed Jan. 11, 2010.

[No Author] www.btc-bti.com/applications/cryogenicstorage.htm, 6 pgs, printed Jan. 11, 2010.

Albrecht et al., "Closure of Osteochondral Lesions Using Chondral Fragments and Fibrin Adhesive," Arch. Orthop. Trauma Surg. 101: 213-217 (1983).

Albrecht. F.H., "The Closure of Joint Cartilage Defects by Means of Cartilage Fragments and Fibrin Adhesive," Fortschr. Med. 101(37):1650-52 (1983).

(56) References Cited

OTHER PUBLICATIONS

Allcock, H.R., The Encyclopedia of Polymer Science, vol. 13, pp. 31-41, Wiley Intersciences, John Wiley & Sons, 1988.
Andreasen et al., Evaluation of different types of autotransplanted connective tissues as potential periodontal ligamant substitues: An experimental replantation study in monkeys, International Journal of Oral Surgery, Jun. 1981, vol. 10, Issue 3, pp. 189-201.(Full text).
Australian Search Report for AU application No. 2006200194, mailed Feb. 4, 2008.
Boland et. al., J. Macromol. Sci.-Pure Appl. Chem., 2001, A38(12), p. 1231-1243).
Bonisch, M., et al. "Septumredonstrucktion mit PDS-Folie" HNO 47: 1999 pp. 546-550.
Buschmann et al., J. Orthop. Res. 1992; 10:745-752.
Caterson EJ., et al. "Three-Dimensional Cartilage Formation by Bone Marrow-Derived Cells Seeded in Polylactide/Alginate Amalgam," J Biomed Mater Res. 57(3):394-403 (2001) (Abstract Only).
Chen G., Ushida T. and Tateishi T. "A hybrid network of synthetic polymer mesh and collagen sponge," Chem. Commun., 2000, 1505-1506.
Cohn et al., Journal of Biomaterials Research, vol. 22, pp. 993-1009, 1988.
Cohn, Polymer Preprints (ACS Division of Polymer Chemistry), vol. 30(1), p. 498, 1989.
De Groot, J.H. et al., "Meniscal tissue regeneration in porous 50/50 copoly(l-lactide/epsilon-caprolactone) implants" Biomaterials, vol. 18, No. 8, 1997, pp. 613-622.
De Groot, J.H. et al., "Use of porous polyurethanes for meniscal reconstruction and meniscal prostheses" Biomaterials, vol. 17, No. 2, 1996, pp. 163-173.
Defrere et al., "Teflon/polyurethane arthroplasty of the knee: the first 2 years preliminary clinical experience in a new concept of artificial resurfacing of full thickness cartilage legions of the knee," Acta Chir. Belg., 1992, vol. 92, No. 5, pp. 217-227.
Deuel, T. et al., "Growth Factors in Principles of Tissue Engineering," Second Edition, Academic Press pp. 129-141 (2000).
Dialog English language abstract for DE 19812195, published Sep. 30, 1999.
Eckersberger, M.D., Franz, "Circumferential tracheal replacement with costal cartilage", The Journal of Thoracic and Cardiovascular Surgery, 1987;94: pp. 175-180.
European Search Report for EP 08075114.2, mailed May 12, 2010.
European Search Report for EP 10075307 mailed Oct. 6, 2010.
European Search Report, for EP 03 25 6522, mailed Feb. 24, 2004.
European Search Report, for EP Application No. 07252617.1, mailed Nov. 2, 2007.
Examination file history of EP 01310810, priority date of Dec. 21, 2000.
Frenkel, S, Ph.D. and Paul E. Di Cesare, M.D., "Degradation and Repair of Articular Cartilage," Frontiers in Bioscience, 4th ed., pp. 671-685, pp. 1-32 (Oct. 15, 1999).
Gooch, K. et al., "Mechanical Forces and Growth Factors Utilized in Tissue Engineering" Frontier in Tissue Engineering, Pergamon Chapter II.3, pp. 61-82 (1998).
Grigolo, B., et al. "Transplantation of Chondrocytes Seeded on a Hyaluronan Derivative (hyaff-11) into Cartilage Defects in Rabbits," Biomaterials 22(17):2417-2424 (2001) (Abstract Only).
Heller: 'Handbook of Biodegradable Polymers', 1997, Hardwood Academic Press pp. 99-118.
Hutmacher DW., "Scaffold Design and Fabrication Technologies for Engineering Tissues—State of the Art and Future Prospectives", J Biomater Sci Polym Ed, 12(1):107-124 (2001) (Abstract Only).
Hutmacher DW., "Scaffolds in Tissue Engineering Bone and Cartilage", Biomaterials, 21(24):2529-2543 (2000) (Abstract Only).
Ibarra, C. M.D. et al. "Tissue-Engineered Meniscus—Cells and Matrix", Tissue Engineering in Orthopedic Surgery 31 (3):411-418 (Jul. 2000).
Ikada, Yoshito, Handbook of Fiber Science and Technology, Edited by Menachem Lewin, Jack Preston, vol. III, Part B, Chapter 8, pp. 253, 289-295, Published by M. Dekker, 1983.
Japanese Office Action issued Apr. 24, 2012 for Application No. 2007-171032 (6 Pages).
Japanese Office Action issued Aug. 28, 2012 for Application No. 2004-233655 (6 Pages).
Japanese Office Action, from JP 2004-191861, mailed Mar. 1, 2011.
Kemnitzer and Kohn, in the Handbook of Biodegradable Polymers, edited by Domb, et. al., Hardwood Academic Press, pp. 251-272 (1997).
Koski, J. M.D. et al., "Meniscal Injury and Repair", Orthopedic Clinics of North American, 31(3):419-435 (Jul. 2000).
Koski, J. M.D. et al., "Tissue-Engineered Ligament—Cells, Matrix, and Growth Factors" Tissue Engineering in Orthopedic Surgery, 31(3):437-452 (Jul. 2000).
Kurashina, K. et al. "Osteogenesis in muscle with composite graft of hydroxyapatite and autogenous calvarial periosteum: a preliminary report" Biomaterials (1995) vol. 16, No. 2, pp. 119-123.
Matsuo, M.D., Kiyoshi et al., "Semiquantitative Correction of Post-traumatic Enophthalmos with Sliced Cartilage Grafts" Plastic and Reconstructive Surgery, vol. 83, No. 3, Postraumatic Enophthalmos, pp. 429-437 (1989).
Megumi, M.D., Yoshikazu, "Augmentation Rhinoplasty with Soft Tissue and Cartilage" Aesthetic Plastic Surgery, 1988, pp. 89-93.
Murray, M., et al. "The Migration of Cells from the Ruptured Human Anterior Cruciate Ligament into Collagen-Glycosaminoglycan Regeneration Templates in Vitro," Biomaterials 22:2393-2402 (2001).
Noishiki Y., "A new trend in hybrid artificial organs" J. Artificial Organs, 1999, vol. 2: pp. 93-96.
Papadopulos, M.D., Angel, "Compound Implant to Project the Nasal Tip" Aesthetic Plastic Surgery, 1987, pp. 181-185.
Partial European Search Report, for EP 04 25 7515, mailed May 9, 2005.
Powers, Dennis L. et al., "A cartilagenous graft as an adjunct to finger joint implant arthroplasty" Journal of Biomedical Materials Research, vol. 19, 1985 pp. 509-518.
Radice, M. "Hyaluronan-Based Biopolymers as delivery vehicles for Bone-Marrow-Derived Mesenchymal Progenitors", J Biomed Mater Res. 50(2):101-9 (2000) (Abstract Only).
Rohrbach, Jens Martin et al., "Biological Corneal Replacement—Alternative to Keratoplasty and Keratoprosthesis? A Pilot Study with Heterologous Hyaline Cartilage in the Rabbit Model", Klin Monatsbl Augenheilkd 207, 1995; pp. 191-196.
Rossi, et al., "Embryonic Purkinje Cells Grafted on the Surface of the Cerebellar Cortex Integrate in the Adult Unlesioned Cerebellum," EP J. Neuroscience 4:589-93 (1992).
Japanese Office Action issued Feb. 26, 2013 for Application No. 2007-171032 (4 Pages).
[No author listed] Warm Glass Disclosure "The Basic Fusing and Slumping Process." 1999. Retrieved from the internet Nov. 22, 2005, 5 pages.
European Search Report for Application No. 04251265.7 issued Jul. 9, 2004.
European Search Report for Application No. 05256123, issued Feb. 1, 2006.
Guy Fortier, Development of Biosensors Based on Immobilization of Enzymes in Eastman AQ Polymer Coated with a Layer of Nation, Analytical Letters, vol. 23 No. 9, Sep. 1990. Abstract.
Lobler et al., Biomaterial implants induce the inflammation marker CPR at the site of implantation, Journal of Biomedical Materials Research, 2002, vol. 61, No. 1, pp. 165-167.

* cited by examiner

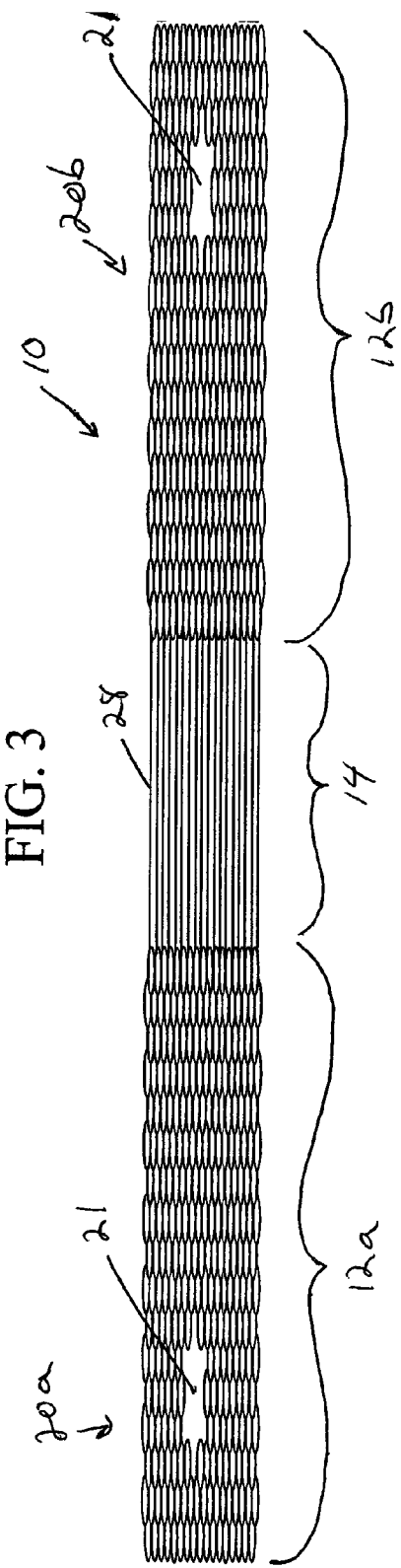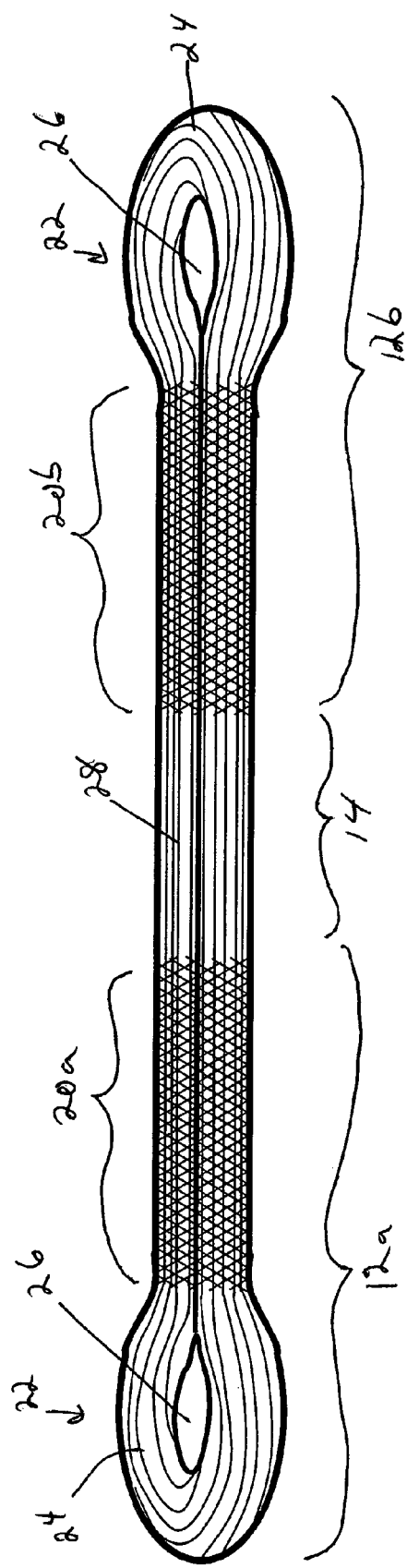

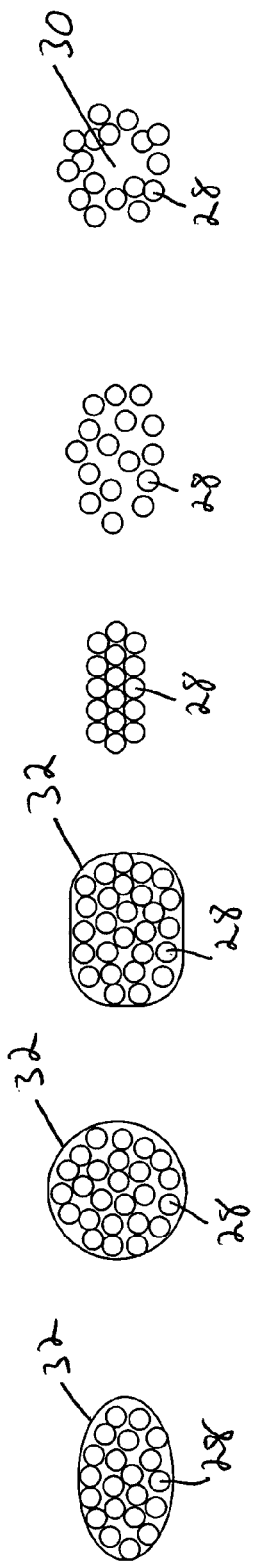
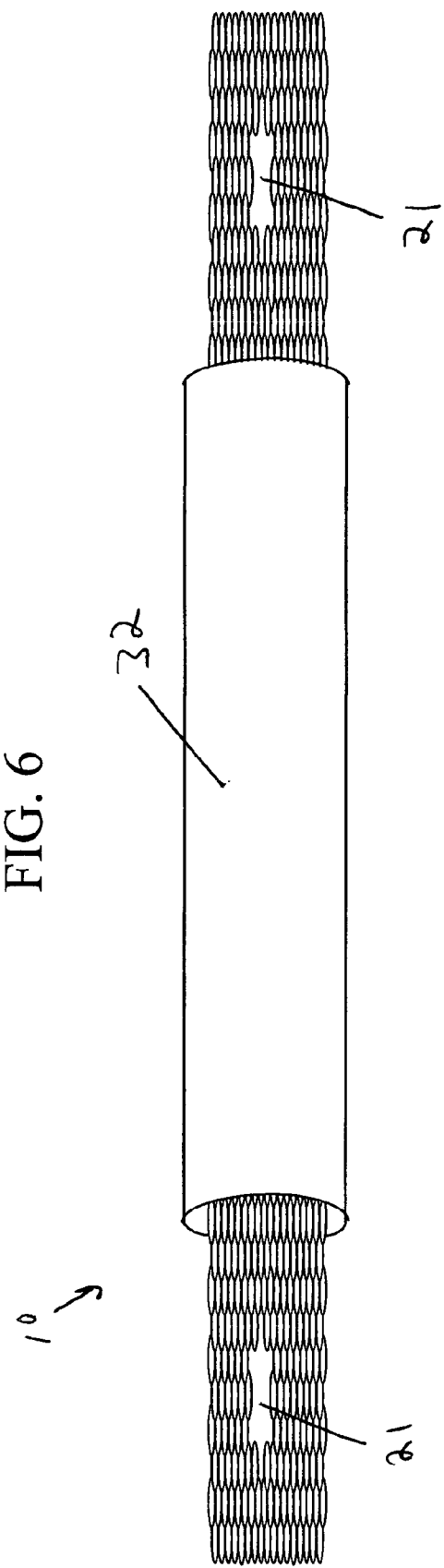

SCAFFOLD FOR CONNECTIVE TISSUE REPAIR

CROSS REFERENCE TO RELATED APPLICATIONS

This application is a divisional of U.S. patent application Ser. No. 10/610,362, filed Jun. 30, 2003, now U.S. Pat. No. 8,226,715, and entitled "SCAFFOLD FOR CONNECTIVE TISSUE REPAIR," which is hereby incorporated by reference in its entirety.

FIELD OF THE INVENTION

This invention relates to prosthetic devices for repairing and replacing torn or damaged connective tissue such as ligaments and tendons.

BACKGROUND OF THE INVENTION

The complete or partial detachment of ligaments, tendons or other soft tissues from their associated bones within the body is a relatively common injury, particularly among athletes. Such injuries generally result from excessive stresses being placed on these soft tissues. For example, a tissue-detaching injury may occur as the result of an accident such as a fall, overexertion during a work-related activity, during the course of an athletic event, or in any one of many other situations and/or activities.

In the case of a partial detachment, commonly referred to under the general term "sprain," the injury will frequently heal itself, if given sufficient time, and if care is taken not to expose the injury to any undue or extraordinary stress during the healing process. If, however, the ligament or tendon is completely detached from its associated bone or bones, or if it is severed as the result of a traumatic injury, partial or permanent disability may result. Fortunately, a number of surgical techniques exist for re-attaching such detached tissues and/or completely replacing severely damaged tissues.

One such technique involves the replacement of the detached tissue using autogeneic tissue grafts harvested from elsewhere in the body. For example, an anterior cruciate ligament in a human knee can be replaced and/or repaired using a patellar tendon autograft or hamstring tendons. The patellar tendon is harvested with a bone block from the tibia, using the center third of the patellar tendon, and bone block from the patella. This graft has the advantage of having high initial strength and having bone plugs that will facilitate fixation. These grafts are implanted by forming bone tunnels through the tibia and/or femur at the points of normal attachment of the anterior cruciate ligament. A patellar tendon graft, with a bone plug on each of its ends, is harvested and sized to fit within the bone tunnels. Suture is then attached to the outer end of each bone plug, and thereafter passed through the femoral and/or tibial bone tunnels. The femoral plug and the tibial plug are then inserted into the appropriate bone tunnel behind the suture. Subsequently, the suture is drawn tight to position the bone plugs in the desired location, and impart the desired degree of tension to the ligament graft. Finally, while holding the bone plugs in position, interference screws, cross-pins or other fixation devices are used to securely lock the bone plug in position. The hamstring tendon grafts are implanted in a similar fashion.

While autogeneic tissue grafts have been successfully used to replace connective tissue, the harvesting procedure, like any medical procedure, has associated risks. Two primary concerns are tissue damage at the harvest site during the removal process and donor site morbidity. Complications in harvest have sometimes resulted in patellar fracture. In other cases, patellofemoral pain is observed due to donor site morbidity. Yet, even when the harvesting procedure is successfully performed, the sample may not provide a sufficient supply of tissue for a graft and/or the tissue may not have the desired quality or consistency. In addition, even with a successful surgery, it is possible for patients to rerupture the graft and require revision surgery. For these reasons, there is a need for an alternative source for tissue grafts, which can provide the properties of an autogenic tissue graft.

One example of an alternative graft is allograft tissue. The advantages of using an allograft include elimination of donor site morbidity and decrease in operating time. However, the graft has potential ability to transmit disease and elicit an immune response. There is also a lack of consistency in mechanical properties of the graft and the supply is limited.

For these reasons, there is a need to develop a connective tissue graft that is terminally sterilized and made from synthetic materials or biologically-derived materials. In the past, the initial results using synthetic prosthetic ligament devices looked promising. However, the long term results, such as those that extend beyond one year, showed the mechanical failure of the these devices. These prostheses have been found to lack sufficient strength and durability to act as a permanent replacement for the lifetime of the patient. Other prostheses, such as some made from synthetic materials, have good physical properties, but can erode or cause bone erosion.

Despite existing technology and techniques, there remains a need for connective tissue implants that can provide an approximation of the natural tissue to be replaced or augmented.

SUMMARY OF THE INVENTION

The present invention generally provides a connective tissue scaffold including opposed first and second anchoring segments formed of a plurality of bioresorbable polymeric fibers oriented in a direction substantially parallel to a longitudinal axis of the scaffold, and a plurality of bioresorbable polymeric fibers oriented in a direction substantially transverse to a longitudinal axis of the scaffold. A central segment positioned between the first and second anchoring segments is formed of a plurality of bioresorbable polymeric fibers oriented in a direction substantially parallel to the longitudinal axis of the scaffold. This structure creates sufficient void space in the central segment to facilitate tissue ingrowth.

The longitudinally and transversely oriented fibers of the anchoring segments can include binding regions where the longitudinal and transverse fibers are interconnected, such as, for example by joining the fibers in a weave pattern. The binding regions may be continuous, or they may be non-continuous such that one or more areas of longitudinally oriented fibers are separated by one or more regions having transversely oriented fibers interwoven with the longitudinally oriented fibers.

The anchoring segments of the present invention can further include eyelets adjacent to the binding regions. The eyelets can be formed by the orientation of the binding regions to form a loop-like or open area that facilitates fixation of the scaffold.

The longitudinal fibers of the of the central segment can run parallel to each other without interconnecting. In addition the fibers of the central segment can be loosely bundled in an annular pattern, such that a centrally formed space exists between the annularly oriented fibers. Alternatively, the longitudinal fibers can be formed in a braid pattern.

The fibers of the scaffold of the present invention are constructed of a bioresorbable polymeric material such as polymers or copolymers formed from monomers selected from the group consisting of lactide, glycolide, dioxanone, and caprolactone.

In another embodiment of the present invention, the scaffold can further include a biocompatible, bioresorbable material covering at least a portion of the first and second anchoring segments and the central segment. The bioresorbable material can be a biological material, for example a naturally occurring extracellular matrix (ECM) material. One such naturally occurring ECM, by way of example, is small intestine submucosa. The bioresorbable material may also be formed over the first and second anchoring segments and the central segment as a wrap, sleeve, or sheath.

The bioresorbable material may be formed over the first and second anchoring eyelets, the first and second binding regions, and the central segment as a wrap, sleeve, or sheath.

In yet another embodiment, the scaffold of the present invention can include at least one minced tissue particle that is associated with at least a portion of the scaffold, such that the minced tissue particles includes an effective amount of viable cells that can migrate out of the minced tissue particle and populate the scaffold. In addition to the at least one minced tissue particle, the scaffold may include an adhesion agent and/or at least one additional biological component.

The invention also provides methods of using the scaffold to repair or replace connective tissue, such as ligaments and tendons.

BRIEF DESCRIPTION OF THE DRAWINGS

FIG. 3 is a schematic view of another embodiment of the connective tissue scaffold;

FIG. 4 is a perspective view of yet another embodiment of the connective tissue scaffold;

FIGS. 5A-5F are cross sectional views of representative central segments of the connective tissue scaffolds of the present invention;

FIG. 6 is schematic view of another embodiment of the connective tissue scaffold of FIG. 3; and FIG. 7 is a perspective view of another embodiment of the connective tissue scaffold of FIG. 4; and.

DETAILED DESCRIPTION OF THE INVENTION

The tissue scaffold of the invention is useful as an implant to replace or augment damaged or torn connective tissue. This scaffold provides an approximation of the natural tissue to be replaced or augmented. The scaffold should have initial mechanical properties similar or greater than those of the native tissue and at the same time support tissue ingrowth and regeneration. Overtime the implant will degrade and become replaced by healthy and functional tissue.

Figure 1:
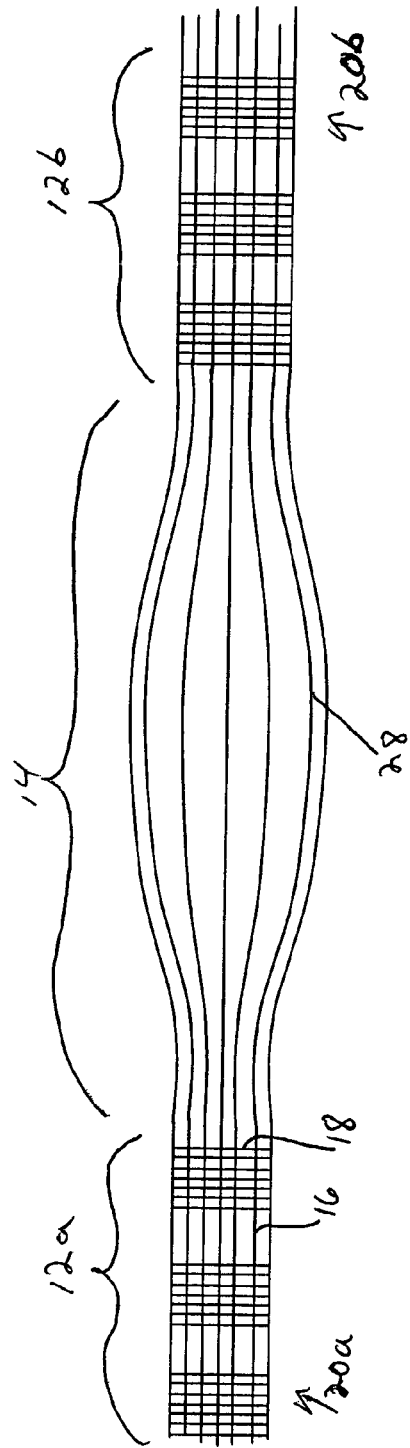
FIG. 1 is a schematic view of one embodiment of the connective tissue scaffold of the present invention.

The present invention generally provides a bioresorbable scaffold 10 for the repair or replacement of connective tissue, such as ligaments or tendons. As shown in FIG. 1, the scaffold 10 includes opposed first and second anchoring segments 12a, 12b which can bind together the fibers of the scaffold and can also receive a tissue fixation device for mating the scaffold 10 within a patient. The scaffold 10 also has a central segment 14, positioned between the anchoring segments 12a, 12b, formed of a plurality of bioresorbable polymeric fibers oriented in a direction substantially parallel to the longitudinal axis of the scaffold.

The scaffold of the present invention is particularly advantageous in that it is preferably made of a bioresorbable polymeric material having sufficient strength to substitute for a tendon or ligament, such as an ACL, and it further allows and encourages regeneration of the failed connective tissue it replaces. In use, the scaffold provides a resorbable, off-the-self replacement for connective tissue which encourages tissue regeneration and results in a native replacement for damaged connective tissue without the drawbacks of autograft implants, allograft implants, and permanent synthetic replacements. Further, by providing an autograft substitute, the bioresorbable scaffold of the present invention eliminates the risks associated with autograft harvesting procedures.

The anchoring segments 12a, 12b of the scaffold 10 of the present invention preferably includes a plurality of fibers 16 oriented in a direction substantially parallel to a longitudinal axis of the scaffold 10 and a plurality of fibers 18 oriented in a direction substantially transverse to a longitudinal axis of the scaffold 10. In one embodiment, the longitudinally oriented fibers 16 ("longitudinal") and transversely oriented ("transverse") fibers 18 form binding regions 20a, 20b which bind together the scaffold 10 at its ends. In one embodiment, the longitudinal and transverse fibers 16, 18 of the binding regions 20a, 20b form a weave pattern with the longitudinal and transverse fibers 16, 18.

In the simplest form, the weave may be constructed such that transverse fibers 18 interlace with the longitudinal fibers 16 by alternating between one side of one longitudinal fiber or group of fibers 16, and an opposite side of an adjacent longitudinal fiber or group of fibers 16. The woven binding regions 20a, 20b may be constructed from a variety of weave patterns which interconnect the longitudinal and transverse fibers 16, 18. One skilled in the art will appreciate that the weave can be constructed based on a number of patterns and can have a variety of characteristics such as weave density, but preferably results in a weave sufficient to bind together the longitudinal and transverse fibers 16, 18.

The transverse fibers can interlock the longitudinal fibers not only in one direction but in two directions so that a three-dimensional woven structure is created. The implant can consist of 40-99% substantially longitudinal direction filaments (x-axis), 1-50% substantially transverse cross direction (y-axis) filaments, and 1-50% substantially transverse z-direction filaments. The warp consists of longitudinal and z-direction filaments and the weft consists of y-direction filaments. A woven structure is desirable because of its wear and abrasion resistance properties. This characteristic is important for ligament reconstruction as this graft is inserted through a bone tunnel which has sharp edges that can scratch the graft.

In addition to weaving the longitudinal and transverse fibers 16, 18 together, the binding regions 20a, 20b can be constructed in a variety of other ways. In one alternative embodiment, at least some of the transverse fibers 18 can be wrapped around the outside of the longitudinal fibers 16 to secure the longitudinal and transverse fibers 16, 18. For example, the transverse fibers 18 may be wrapped around the longitudinal fibers 16 to form a knot or whipping. One skilled in the art will appreciate that there are a variety of ways to form a whipping such as, for example an American Whipping, a Sailmaker's Whipping, a West Country Whipping, etc. While the styles vary, whippings work on the same principle; the transverse fiber (or fibers) 18 is tightly wound around the longitudinal fibers 16, while the ends of the transverse fiber 18 are secured by a knot or by tucking. Although a whipping is preferably formed by wrapping a transverse fiber (or fibers) 18 around a bundle containing all the longitudinal fibers 16, the longitudinal fibers 16 may be grouped into smaller bundles and whipped. In one embodiment, the longitudinal fibers 16 may be whipped together in a large bundle and additional whippings may be used adjacent to the large bundle. Further, the adjacent whippings may include smaller bundles of the longitudinal fibers 16.

In yet a further embodiment, the longitudinal and transverse fibers 16, 18 of the binding regions 20a, 20b may be interconnected by stitching. The longitudinal fibers 16 can be grouped into a bundle and the transverse fibers 18 can be repeatedly led through the bundle and pulled tight to secure the binding regions 20a, 20b. Further, a three dimensional weave may be simulated or replicated by sewing together two or more plies of two-dimensional weaves. Braiding and/or knitting may also be used to interconnect filaments. A person skilled in the art will appreciate that the transverse 18 and longitudinal fibers 16 can be interconnected by a variety of other techniques. In still yet another embodiment, the fibers of the binding regions 20a, 20b may be interconnected by physically bonding the longitudinal fibers 16 with the transverse fibers 18, or physically bonding the fibers with another agent such as, for example, an adhesive or a polymer. Filaments may also be bonded via thermal methods, including but not limited to ultrasonic bonding, infrared bonding, laser bonding, or application of the filaments to a heated electrical surface. Filaments may also be bonded via chemical means, including but not limited to solvent bonding. Filaments may also be bonded the application of suitable adhesives, including but not limited to those that are bioabsorbable and non-bioabsorbable. Finally, combinations of the above techniques may be used to interconnect or bond fibers or filaments. In addition, the fibers may be interconnected as discussed above, and then physically bound to increase the mechanical strength of the connection.

Figure 2:
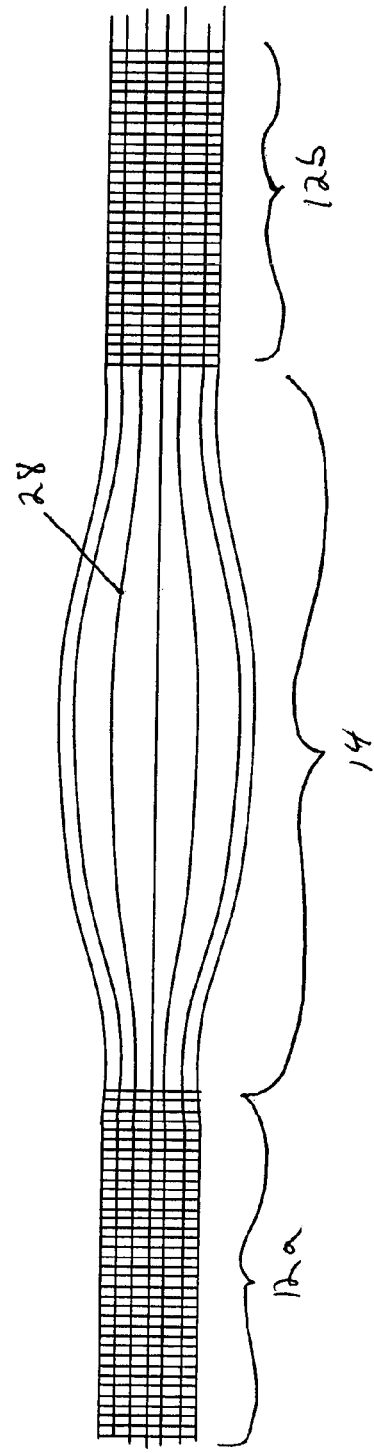
FIG. 2 is a schematic view of another embodiment of the connective tissue scaffold.

Regardless of the method of interconnection, the binding regions 20a, 20b may be broken down into several parts, such that the binding regions are not continuous. As illustrated in FIG. 1, for example, the binding regions 20a, 20b can alternate between areas of interconnected longitudinal and transverse fibers 16, 18 and areas of only longitudinal fibers 16. In another embodiment, illustrated in FIG. 2, each binding region 20a, 20b can be formed of continuous zones of longitudinal and transverse fibers 16, 18.

One property contributed by the interconnection of the longitudinal and transverse fibers 16, 18 is that the binding regions 20a, 20b are preferably interconnected to minimize laxity and achieve stiffness similar to that of native tissue. Elastic modulus is a property that varies based on the identity of materials used to construct the fibers and on the technique used to interconnect the longitudinal and transverse fibers 16, 18. Preferably, for cruciate ligament repair, the stiffness of the binding regions 20a, 20b of the graft is higher than 100 N/mm and preferably higher than 150 N/mm.

One function of the binding regions 20a, 20b is to enable the scaffold 10 to be anchored within a patient, such as by receiving a tissue fixation device. A tissue fixation device can affix or anchor the scaffold 10 by extending through the scaffold 10 and/or creating an interference fit between the scaffold 10 and a tissue region. Exemplary tissue fixation devices which can be used with the scaffold 10 of the present invention include screws, sutures, staples, pins, buttons, and combinations thereof.

The binding regions 20a, 20b may be configured to form a receiving area 21 for receiving a tissue fixation device as shown in FIG. 3. The receiving area 21 may be created by the weaving, whipping, knitting, or stitching of the longitudinal and transverse fibers 16, 18 to create an open area devoid of fibers or an areas of reduced fiber density. In use, the tissue fixation device can then be pushed through a binding region or binding regions to fix the scaffold to tissue.

In one embodiment, each anchoring segment 12a, 12b can include an eyelet 22 as illustrated in FIG. 4. A suitable eyelet 22 can be formed by a group of fibers extending from a binding region to create a loop 24 around an open area 26. Preferably, the open area 26 of the eyelet 22 is appropriately sized to receive a tissue fixation device such as a tissue fixation pin. The open area 26 of the eyelet 22 can be used alone or in conjunction with a suture to tension the graft during fixation.

In a preferred embodiment, at least one of the anchoring segments 12a, 12b will be affixed within a bone tunnel, such as a femoral and/or a tibial bone tunnel. Therefore the anchoring segments 12a, 12b should be suitably sized to fit within such a bone tunnel. Preferably, the length of the anchoring segments 12a, 12b will be approximately equal to or less than the length of a bone tunnel, for example in the range of about 10 mm to 80 mm, and more preferably in the range of about 20 mm to 60 mm. Similarly, the diameter of the anchoring segments 12a, 12b should also be adapted to fit within a bone tunnel. The diameter of the anchoring segments 12a, 12b can be in the range of about 2 mm to 15 mm.

As noted above, the scaffold 10 of the present invention also has a central segment 14 disposed between the anchoring segments 12a, 12b. The central segment 14 includes longitudinally oriented fibers 28 which may or may not be interconnected. The central segment 14 is intended to provide the functionality of the connective tissue which it replaces. For example, if the scaffold 10 is used as a replacement for an anterior cruciate ligament, the fibers 28 of the central segment 14 provide the properties of the native ligament and have the properties to support tissue ingrowth.

The central segment 14 preferably has sufficient length to replace the connective tissue for which it substitutes. A person skilled in the art will appreciate that the length of the central segment 14 will vary depending on the size of the patient and the intended use of the scaffold 10. For example, one skilled in the art will realize that the sizes will vary greatly for use of this implant in anterior cruciate ligament repair, posterior cruciate ligament repair or flexor tendon repair.

In one embodiment, the fibers 28 of the central segment 14 do not interconnect with each other and run between the anchoring segments 12a, 12b in bundle of substantially longitudinally oriented fibers 28. FIGS. 5A-5F illustrate exemplary cross sections of the central segment 14, such as, for example, an oval shape (FIG. 5A), a circular shape (FIG. 5B), a rectangular shape (FIGS. 5C, 5D) and an irregular shape (FIG. 5E). In addition, the longitudinal fibers 28 of the central segment may be tightly packed FIG. 5D or loosely grouped FIG. 5E-5F.

Where the longitudinal fibers 28 of the central segment 14 are loosely grouped, they may be oriented in an annular pattern such that collectively the longitudinal fibers define a central space 30 as illustrated in FIG. 5F. The annular pattern may be formed in a variety of ways such as by imparting a slight twist to the longitudinal fibers 28 before binding them in the binding regions 20a, 20b. An exemplary twist of the longitudinal fibers 28 between the anchoring segments 12a, 12b may be in the range of about 0° and 720°.

The fibers 28 of the central segment 14 may alternatively be interconnected with one another. For example, the longitudinal fibers 28 may be loosely braided or twisted together along the central segment 14. A variety of braid patterns may be used. For example the longitudinal fibers 28 of the central region 14 may be grouped into several bundles and the bundles may be braided. The braid pattern preferably orients the fibers 28 of the central segment 14 in an organized pattern.

The interconnection of the fibers 28 of the central segment 14 are characterized by increased flexibility with respect to the binding regions 20a, 20b. The improved flexibility is due to the lower fiber density of the central segment 14 because the fibers are not packed and restrained. The fibers preferably have some degree of motion, especially under cyclic load, to move and allow void space or porosity to be created within the central segment. Preferably, the minimum amount of void space will be approximately 14% by volume. The increased density of the binding regions 20a, 20b is based on including not only longitudinal fibers 16 but also transverse fibers 18, and the longitudinal and transverse fibers 16, 18 being tightly bound together, such as, for example in a hexagonally close packed structure.

In addition to providing physical properties and functionality that mimics that of a natural ligament or tendon. The central segment 14 provides a region that receives and retains any tissue fragments, cells, or bioactives that may be incorporated into the scaffold 10 to initiate regrowth and replacement of a natural ligament or tendon. The lower fiber density allows tissue fragments or cells to be retained within the scaffold 10, and to populate the scaffold 10. Where the fibers 28 of the central segment 14 are configured in an annular pattern to form a central space 30, tissue fragments, cells or bioactives may be seeded within the central space 30. The segments 12a and 12b can also receive and retain tissue fragments, cells, or bioactives to enhance bone repair and integration of graft with host tissue.

The terms "longitudinal" and "transverse", as used herein, indicate the overall direction in which the fibers (16, 18, 28) are traveling, and include substantially longitudinal and transverse fibers such as those shown in FIGS. 3-4. Acceptable variation from the longitudinal and transverse orientation include, by non-limiting example, those variations created by interconnecting the fibers or imparting the fibers with a twist. For example, a longitudinal fiber extending from one end of the scaffold to the other may dip and rise as it encounters other fibers in a braid or weave, but overall the fiber extends in the longitudinal direction and travels on a path substantially parallel to adjacent fibers traveling in the longitudinal direction.

The scaffold is preferably made of a biocompatible, bioresorbable material so that after implantation into a patient to replace or repair connective tissue, the scaffold gradually degrades over time. When first implanted, the scaffold preferably has a tensile strength and elastic modulus similar to that of native connective tissue, such as, for example a ligament. The preferred tensile strength of the scaffold for an anterior cruciate ligament or a posterior cruciate ligament in the longitudinal direction is between about 500N and 4000N, and more preferably, between about 1000N and 2500N. The preferred stiffness of the scaffold is between about 50N/m and 300N/m, and more preferably, between about 100N/m and 200N/m. As the fibers of the scaffold resorb and are replaced by natural tissue, the strength of the fibers may diminish. Therefore, the resorption profile of the scaffold should be sufficiently long to reinforce and provide structure to tissue during the regeneration process. A person skilled in the art can determine a suitable resorption profile, depending on the desired use of the scaffold, and can tailor the resorption profile by varying the materials used to construct the scaffold. Preferably, the scaffold has a slow resorption profile, such that resorption requires at least three months, preferably more than six months, and even more preferably, at least ten months.

In one embodiment of the present invention, the fibers of the scaffold can be formed from a biocompatible polymer. A variety of biocompatible polymers can be used to make the fibers according to the present invention including synthetic polymers, natural polymers or combinations thereof. As used herein the term "synthetic polymer" refers to polymers that are not found in nature, even if the polymers are made from naturally occurring biomaterials. The term "natural polymer" refers to polymers that are naturally occurring. In embodiments where the fibers of the scaffold include at least one synthetic polymer, suitable biocompatible synthetic polymers can include polymers selected from the group consisting of aliphatic polyesters, poly(amino acids), copoly(ether-esters), polyalkylene oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polyurethanes, poly(ether urethanes), poly(ester urethanes), poly (propylene fumarate), poly(hydroxyalkanoate) and blends thereof. Suitable synthetic polymers for use in the present invention can also include biosynthetic polymers based on sequences found in collagen, elastin, thrombin, silk, keratin, fibronectin, starches, poly(amino acid), gelatin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides and combinations thereof.

For the purpose of this invention aliphatic polyesters include, but are not limited to, homopolymers and copolymers of lactide (which includes lactic acid, D-, L- and meso lactide); glycolide (including glycolic acid); ε-caprolactone; p-dioxanone (1,4-dioxan-2-one); trimethylene carbonate (1,3-dioxan-2-one); alkyl derivatives of trimethylene carbonate; δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one and polymer blends thereof. Additional exemplary polymer or polymer blends include, by non-limiting example, a polydioxanone, a polyhydroxybutyrate-co-hydroxyvalerate, polyorthocarbonate, a polyaminocarbonate, and a polytrimethylene carbonate. Aliphatic polyesters used in the present invention can be homopolymers or copolymers (random, block, segmented, tapered blocks, graft, triblock, etc.) having a linear, branched or star structure. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g., PEO/PLA). Polyalkylene oxalates, for the purpose of this invention, include those described in U.S. Pat. Nos. 4,208, 511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and, -caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al., Hardwood Academic Press, pp. 161-182 (1997). Polyanhydrides include those derived from diacids of the form HOOC—$C_6H_4$—O—$(CH_2)_m$—O—$C_6H_4$—COOH, where "m" is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al., Hardwood Academic Press, pp. 99-118 (1997).

As used herein, the term "glycolide" is understood to include polyglycolic acid. Further, the term "lactide" is understood to include L-lactide, D-lactide, blends thereof, and lactic acid polymers and copolymers.

Elastomeric copolymers are also particularly useful in the present invention, including, but are not limited to, elastomeric copolymers of ε-caprolactone and glycolide (including polyglycolic acid) with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of ε-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Examples of suitable biocompatible elastomers are described in U.S. Pat. No. 4,045,418.

In one embodiment, the elastomer is a copolymer of 35:65 ε-caprolactone and glycolide, formed in a dioxane solvent. In another embodiment, the elastomer is a copolymer of 40:60 ε-caprolactone and lactide. In yet another embodiment, the elastomer is a 50:50 blend of a 35:65 copolymer of ε-caprolactone and glycolide and 40:60 copolymer of ε-caprolactone and lactide.

The fibers of the present invention can, optionally, be formed from a bioresorbable or bioabsorbable material that has the ability to resorb in a timely fashion in the body environment. The differences in the absorption time under in vivo conditions can also be the basis for combining two different copolymers when forming the fibers of the present invention. For example, a copolymer of 35:65 ε-caprolactone and glycolide (a relatively fast absorbing polymer) can be blended with 40:60 ε-caprolactone and L-lactide copolymer (a relatively slow absorbing polymer) to form a biocompatible fiber. Depending upon the processing technique used, the two constituents can be either randomly inter-connected bicontinuous phases, or the constituents could have a gradient-like architecture with a well integrated interface between the two constituent layers.

In an exemplary embodiment, the fibers of the present invention are made from a 95:5 copolymer of lactide and glycolide such as PANACRYL, available from Ethicon, Inc.

In one embodiment, it is desirable to use polymer blends to form fibers which transition from one composition to another composition in a gradient-like architecture. Scaffolds having this gradient-like architecture are particularly advantageous in tissue engineering applications to repair or regenerate the structure of naturally occurring tissue such as cartilage (articular, meniscal, septal, tracheal, auricular, costal, etc.), tendon, ligament, nerve, esophagus, skin, bone, and vascular tissue. Clearly, one skilled in the art will appreciate that other polymer blends may be used for similar gradient effects, or to provide different gradients (e.g., different absorption profiles, stress response profiles, or different degrees of elasticity). For example, such design features can establish a concentration gradient for the suspension of minced tissue associated with the prostheis of the present invention, such that a higher concentration of the tissue fragments is present in one region of the scaffold (e.g., an interior portion) than in another region (e.g., outer portions).

The gradient-like transition between compositions can also be oriented in the radial direction of the fibers. For example, some of the fibers of the scaffold may be co-extruded to produce a fiber with a sheath/core construction. Such fibers are comprised of a sheath of biodegradable polymer that surrounds one or more cores comprised of another biodegradable polymer. Fibers with a fast-absorbing sheath surrounding a slower-absorbing core may be desirable for extended support.

In another embodiment, the fibers can be made of a bioabsorbable glass. Bioglass, a silicate containing calcium phosphate glass, or calcium phosphate glass with varying amounts of solid particles added to control resorption time are examples of materials that could be spun into glass fibers and used for the reinforcing material. Suitable solid particles that may be added include iron, magnesium, sodium, potassium, and combinations thereof.

In embodiments where the fibers includes at least one natural polymer, suitable examples of natural polymers include, but are not limited to, fibrin-based materials, collagen-based materials, hyaluronic acid-based materials, glycoprotein-based materials, cellulose-based materials, silks and combinations thereof. By way of nonlimiting example, the biocompatible scaffold 10 can be constructed from a collagen-based small intestine submucosa.

In another embodiment of the present invention, a biocompatible ceramic material can be incorporated into the anchoring segments 12*a* and 12*b* of the scaffold. Suitable biocompatible ceramic materials include, for example, hydroxyapatite, α-tricalcium phosphate, β-tricalcium phosphate, bioactive glass, calcium phosphate, calcium sulfate, calcium carbonate, xenogeneic and allogeneic bone material and combinations thereof. Suitable bioactive glass materials for use in the present invention include silicates containing calcium phosphate glass, or calcium phosphate glass with varying amounts of solid particles added to control resorption time. Suitable compounds that may be incorporated into the calcium phosphate bioactive glass include, but are not limited to, magnesium oxide, sodium oxide, potassium oxide, and combinations thereof.

One skilled in the art will appreciate that the selection of a suitable material for forming the biocompatible fibers of the present invention depends on several factors. These factors include in vivo mechanical performance; cell response to the material in terms of cell attachment, proliferation, migration and differentiation; biocompatibility; and optionally, bioabsorption (or bio-degradation) kinetics. Other relevant factors include the chemical composition, spatial distribution of the constituents, the molecular weight of the polymer, and the degree of crystallinity.

In a further embodiment of the present invention, the scaffold 10 can include bioresorbable fibers of different compositions. The fibers may be selected to create a complementary mixture of fibers having different properties, or fibers having a different composition may be added to the scaffold 10 to perform a specific job, such as for example, cell adhesion. In one embodiment, the longitudinal fibers can be constructed of a different material from the transverse fibers, and preferably have a longer resorption profile.

In addition to the longitudinal and transverse bioresorbable fibers, the scaffold of the present invention can further include at least one sample of viable tissue that is associated with at least a portion of the scaffold. The term "viable," as used herein, refers to a tissue sample having one or more viable cells. Virtually any type of tissue can be used to construct the tissue repair scaffolds of the present invention. Preferably, the tissue used is selected from cartilage tissue, meniscal tissue, ligament tissue, tendon tissue, skin tissue, bone tissue, muscle tissue, periosteal tissue, pericardial tissue, synovial tissue, nerve tissue, fat tissue, kidney tissue, bone marrow, liver tissue, small intestine tissue, bladder tissue, pancreas tissue, spleen tissue, intervertebral disc tissue, embryonic tissue, periodontal tissue, vascular tissue, blood and combinations thereof. The tissue used to construct the tissue scaffolds can be autogeneic tissue, allogeneic tissue, or xenogeneic tissue.

Where the scaffold 10 is useful for ligament or tendon repair, the tissue incorporated into the central segment is preferably bone-free tissue selected from the group consisting of tendon tissue, ligament tissue of the same type that is to be repaired, ligament tissue of a different type than the tissue that is to be repaired, synovial tissue, periosteal tissue, cartilage tissue, meniscus tissue, fascia, skin, and combinations thereof. In one embodiment, bone tissue fragments may be is applied to the anchoring segments 12a, 12b. For example, during the formation of the tibial and femoral bone tunnels for cruciate repair, an instrument, i.e. a coring reamer, can be used to harvest the bone from the site. This cored bone then can be used in its entirety or in fragments and placed alongside the anchoring segments 12a, 12b.

The tissue can be obtained using any of a variety of conventional techniques, such as for example, by biopsy or other surgical removal. Preferably, the tissue sample is obtained under aseptic conditions. Once a sample of living tissue has been obtained, the sample can then be processed under sterile conditions to create a suspension having at least one minced, or finely divided, tissue particle. The particle size of each tissue fragment can vary, for example, the tissue size can be in the range of about 0.1 and 30 mm$^3$, but preferably the tissue particle is less than 10 mm$^3$. The shape of the tissue fragments do not need to be isotropic (i.e., cubic or spherical), instead the tissue fragments can be in the form of strips or sheets of tissue such that one dimension of the tissue is equal to or less than 1 mm in thickness.

Preferably, the minced tissue has at least one viable cell that can migrate from the tissue fragment onto the scaffold. More preferably, the tissue contains an effective amount of cells that can migrate from the tissue fragment and begin populating the scaffold 10. In an optional embodiment, the minced tissue fragments may be contacted with a matrix-digesting enzyme to facilitate cell migration out of the extracellular matrix surrounding the cells. The enzymes are used to increase the rate of cell migration out of the extracellular matrix and into the scaffold. Suitable matrix-digesting enzymes that can be used in the present invention include, but are not limited to, collagenase, chondroitinase, trypsin, elastase, hyaluronidase, petidase, thermolysin and protease.

In one embodiment, the minced tissue particles can be formed as a suspension in which the tissue particles are associated with a physiological buffering solution. Suitable physiological buffering solutions include, but are not limited to, saline, phosphate buffer solution, Hank's balanced salts, Tris buffered saline, Hepes buffered saline and combinations thereof. In addition, the tissue can be minced in any standard cell culture medium known to those having skill in the art, either in the presence or absence of serum. Prior to depositing the suspension of minced tissue on the scaffold or at the site of implantation, the minced tissue suspension can be filtered and concentrated, such that only a small quantity of physiological buffering solution remains in the suspension to prevent the tissue particles from drying out, and the minced tissue particles can be directly applied to the scaffold or site of implantation. Preferably, the minced tissue particles are loaded at a concentration in the range of approximately 1 to 100 mg/cm$^2$, and more preferably in the range of about 1 to 20 mg/cm$^2$.

The suspension of minced living tissue can be used to create a connective tissue scaffold according to the present invention by depositing the suspension of living tissue upon the scaffold, such that the tissue and the scaffold become associated. Preferably, the tissue is associated with at least a portion of the scaffold. Additionally, the scaffold can be implanted in a subject immediately, or alternatively, the tissue seeded scaffold can be incubated under sterile conditions for a duration and under conditions that are effective to maintain the viability of the tissue sample. In embodiments where the construct is incubated, the incubation conditions can vary, but preferably, the scaffold is incubated for a duration in the range of 1 hour to 6 weeks, and more preferably between about 1 week and 6 weeks, at a temperature in the range of about 20 to 40° C., and in an atmosphere containing between about 5 and 10% carbon dioxide ($CO_2$) and high humidity, e.g., approximately 100% humidity.

A kit can be used to assist in the preparation of the tissue scaffold of the present invention. According to the present invention, the kit includes a sterile container that houses one or more biocompatible scaffolds, a harvesting tool for collecting the living tissue sample from a subject, and one or more reagents for sustaining the viability of the tissue sample. Suitable reagents for sustaining the viability of the tissue sample include a physiological solution, such as for example, saline, phosphate buffering solution, Hank's balanced salts, standard cell culture medium, Dulbecco's modified Eagle's medium, ascorbic acid, HEPES, nonessential amino acid, L-proline, fetal bovine serum, autologous serum, and combinations thereof. The kit can also include a processing tool for dividing the tissue into minced tissue particles, or alternatively, the harvesting tool can be adapted to collect the tissue sample and to process the sample into finely divided tissue particles. The kit can, optionally, also include a delivery device for transferring the scaffold from the sterile container to a subject for implantation.

A biological component may, optionally, be incorporated within the tissue scaffolds of the present invention. Preferably, the biological component is incorporated within, or coated on, the scaffolds disclosed above. In embodiments where the biological component is coated onto the scaffold, the biological component is preferably associated with at least a portion of the scaffold. By way of nonlimiting example, the biocompatible scaffold can include an adhesion agent for anchoring the suspension of minced tissue fragments to the scaffold. Preferably, the adhesion agent is an anchoring agent, a cross-linking agent (i.e., chemical or physical), and combinations thereof.

Suitable anchoring agents include, but are not limited to, hyaluronic acid, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

Suitable cross-linking agents include, for example, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light (e.g., blue light and UV light), pH, temperature, and combinations thereof.

The biological components used in the present invention can also be selected from among a variety of effectors that, when present at the site of injury, promote healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED and Surgicel®, available from Ethicon, Inc.), hyaluronic acid, and compounds or agents that suppress the immune system (e.g., immunosuppressants).

By way of example, other types of effectors present within the scaffold of the present invention can include heterologous or autologous growth factors, proteins (including matrix proteins), peptides, antibodies, enzymes, platelets, glycoproteins, hormones, cytokines, glycosaminoglycans, nucleic acids, analgesics, viruses, virus particles, and cell types. It is understood that one or more effectors of the same or different functionality may be incorporated within the scaffold.

Examples of suitable effectors include the multitude of heterologous or autologous growth factors known to promote healing and/or regeneration of injured or damaged tissue. These growth factors can be incorporated directly into the scaffold, or alternatively, the scaffold can include a source of growth factors, such as for example, platelets. "Bioactive agents" include one or more of the following: chemotactic agents; therapeutic agents (e.g., antibiotics, steroidal and non-steroidal analgesics and anti-inflammatories, anti-rejection agents such as immunosuppressants and anti-cancer drugs); various proteins (e.g., short term peptides, bone morphogenic proteins, glycoprotein and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), IGF-I, IGF-II, TGF-β I-III, growth and differentiation factors, vascular endothelial growth factors (VEGF), fibroblast growth factors (FGF), platelet derived growth factors (PDGF), insulin derived growth factor (IGF) and transforming growth factors, parathyroid hormone, parathyroid hormone related peptide, bFGF; TGFβ superfamily factors; BMP-2; BMP-4; BMP-6; BMP-12; sonic hedgehog; GDF5; GDF6; GDF8; MP52, CDMP1); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. Suitable effectors likewise include the agonists and antagonists of the agents noted above. The growth factor can also include combinations of the growth factors listed above. In addition, the growth factor can be autologous growth factor that is supplied by platelets in the blood. In this case, the growth factor from platelets will be an undefined cocktail of various growth factors. If other such substances have therapeutic value in the orthopaedic field, it is anticipated that at least some of these substances will have use in the present invention, and such substances should be included in the meaning of "bioactive agent" and "bioactive agents" unless expressly limited otherwise.

"Biologically derived agents" include one or more of the following: bone (autograft, allograft, and xenograft) and derivates of bone; cartilage (autograft, allograft and xenograft), including, for example, meniscal tissue, and derivatives; ligament (autograft, allograft and xenograft) and derivatives; derivatives of intestinal tissue (autograft, allograft and xenograft), including for example submucosa; derivatives of stomach tissue (autograft, allograft and xenograft), including for example submucosa; derivatives of bladder tissue (autograft, allograft and xenograft), including for example submucosa; derivatives of alimentary tissue (autograft, allograft and xenograft), including for example submucosa; derivatives of respiratory tissue (autograft, allograft and xenograft), including for example submucosa; derivatives of genital tissue (autograft, allograft and xenograft), including for example submucosa; derivatives of liver tissue (autograft, allograft and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also intended to be included within "biologically derived agents." If other such substances have therapeutic value in the orthopaedic field, it is anticipated that at least some of these substances will have use in the present invention, and such substances should be included in the meaning of "biologically-derived agent" and "biologically-derived agents" unless expressly limited otherwise.

"Biologically derived agents" also include bioremodelable collageneous tissue matrices. The expressions "bioremodelable collagenous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, whatever the source. Although "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers.

The proteins that may be present within the scaffold can include proteins that are secreted from a cell or other biological source, such as for example, a platelet, which is housed within the scaffold, as well as those that are present within the scaffold in an isolated form. The isolated form of a protein typically is one that is about 55% or greater in purity, i.e., isolated from other cellular proteins, molecules, debris, etc. More preferably, the isolated protein is one that is at least 65% pure, and most preferably one that is at least about 75 to 95% pure. Notwithstanding the above, one skilled in the art will appreciate that proteins having a purity below about 55% are still considered to be within the scope of this invention. As used herein, the term "protein" embraces glycoproteins, lipoproteins, proteoglycans, peptides, and fragments thereof. Examples of proteins useful as effectors include, but are not limited to, pleiotrophin, endothelin, tenascin, fibronectin, fibrinogen, vitronectin, V-CAM, I-CAM, N-CAM, selectin, cadherin, integrin, laminin, actin, myosin, collagen, microfilament, intermediate filament, antibody, elastin, fibrillin, and fragments thereof.

Glycosaminoglycans, highly charged polysaccharides which play a role in cellular adhesion, may also serve as effectors according to the present invention. Exemplary glycosaminoglycans useful as effectors include, but are not limited to, heparan sulfate, heparin, chondroitin sulfate, dermatan sulfate, keratan sulfate, hyaluronan (also known as hyaluronic acid), and combinations thereof.

The scaffold of the present invention can also have cells incorporated therein. Suitable cell types that can serve as effectors according to this invention include, but are not limited to, osteocytes, osteoblasts, osteoclasts, fibroblasts, fibrochondrocytes, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal cells, epithelial cells, myoblasts, tenocytes, ligament fibroblasts, neurons, and bone marrow cells, synoviocytes, embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited. Cells typically have at their surface receptor molecules which are responsive to a cognate ligand (e.g., a stimulator). A stimulator is a ligand which when in contact with its cognate receptor induce the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins). This cellular messenger can be an antibody (e.g., secreted from plasma cells), a hormone, (e.g., a paracrine, autocrine, or exocrine hormone), a cytokine, or natural or synthetic fragments thereof.

The scaffold of the invention can also be used in gene therapy techniques in which nucleic acids, viruses, or virus particles deliver a gene of interest, which encodes at least one gene product of interest, to specific cells or cell types. Accordingly, the biological effector can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once the applicable nucleic acids and/or viral agents (i.e., viruses or viral particles) are incorporated into the scaffold, and can then be implanted into a particular site to elicit a type of biological response. The nucleic acid or viral agent can then be taken up by the cells and any proteins that they encode can be produced locally by the cells. In one embodiment, the nucleic acid or viral agent can be taken up by the cells within the tissue fragment of the minced tissue suspension, or, in an alternative embodiment, the nucleic acid or viral agent can be taken up by the cells in the tissue surrounding the site of the injured tissue. One skilled in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are often used to accomplish such an expression blocking function, which is also known as gene expression knock out.

One skilled in the art will appreciate that the identity of the biological component may be determined by a surgeon, based on principles of medical science and the applicable treatment objectives.

The biological component or effector of the scaffold can be incorporated before or after manufacture of the scaffold, or before or after the surgical placement of the scaffold.

Prior to surgical placement, the scaffold can be placed in a suitable container comprising the biological component. After an appropriate time and under suitable conditions, the scaffold will become impregnated with the biological component. Alternatively, the biological component can be incorporated within the scaffold by, for example, using an appropriately gauged syringe to inject the biological agent(s) into the scaffold. Other methods well known to those skilled in the art can be applied in order to load a scaffold with an appropriate biological component, such as mixing, pressing, spreading, centrifuging and placing the biological component into the scaffold. Alternatively, the biological component can be mixed with a gel-like carrier prior to injection into the scaffold. The gel-like carrier can be a biological or synthetic hydrogel, including an alginate, a cross-linked alginate, hyaluronic acid, collagen gel, fibrin glue, fibrin clot, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycanspoly(N-isopropylacrylamide), poly(oxyalkylene), a copolymer of poly(ethylene oxide)-poly(propylene oxide), poly(vinyl alcohol) and combinations thereof.

Following surgical placement, a scaffold devoid of any biological component can be infused with biological agent (s), or a scaffold that includes at least one biological component can be augmented with a supplemental quantity of the biological component. One method of incorporating a biological component within a surgically installed scaffold is by injection using an appropriately gauged syringe.

The amount of the biological component included with a biocompatible scaffold will vary depending on a variety of factors, including the size of the scaffold, the material from which the scaffold is made, the density of the scaffold, the identity of the biologically component, and the intended purpose of the tissue scaffold. One skilled in the art can readily determine the appropriate quantity of biological component to include within the scaffold for a given application in order to facilitate and/or expedite the healing of tissue. The amount of biological component will, of course, vary depending upon the identity of the biological component and the given application.

In another embodiment, the scaffold can include an additional retaining element that is placed over the tissue-laden scaffold. Preferably, in this embodiment, at least a portion of the tissue suspension is associated with at least a portion of the outer surface of the scaffold, such that the tissue suspension is "sandwiched" between the scaffold and the retaining element. The retaining element can be formed from virtually any biocompatible material, and in one embodiment, the retaining element can be formed using tissue grafts, including grafts obtained from allogeneic tissue, autogeneic tissue, and xenogeneic tissue, an additional biocompatible material selected from the biocompatible materials disclosed above, and combinations thereof. In another embodiment, the retaining element can be a porous mesh, a porous mesh-like material, such as for example, a knit, a weave, a nonwoven, or a thin, perforated elastomeric sheet having pores or perforations to allow tissue ingrowth. The thin, perforated elastomeric sheets are preferably constructed from collagen or silk or blends or copolymers of polylactic acid (PLA), polyglycolic acid (PGA), polycaprolactone (PCL) and polydioxanone (PDO). The type of retaining element used can vary according to the desired tissue repair. By way of non-limiting example, in one embodiments for ACL repair, the retaining element can be a mesh structure. In embodiments where the retaining element is an allograft or an autograft, preferably the allograft or autograft is selected from periosteum, perichondrium, iliotibial band or fascia lata, gracilis tendon, semitendinosis tendon, patellar tendon, synovium and combinations thereof. In embodiments where the retaining element is a xenograft, the xenograft is preferably selected from the corresponding anatomical structure for small intestine, periosteum, perichondrium, iliotibial band or fascia lata, gracilis tendon, semitendonous tendon, patellar tendon, synovium, and combinations thereof. These retaining elements can be placed over the scaffold 10, or alternatively, the retaining element can be affixed, such as for example, by suturing or stapling, the scaffold 10 to act as a retaining element. One skilled in the art will appreciate that additional processing of the retaining element, such as for example, the placement of holes within the retaining element, may be determined by a surgeon, based on principles of medical science and the applicable treatment objectives.

In one embodiment, the retaining element is an electrostatically spun fabric added to the scaffold to act as a barrier to hyperplasia and tissue adhesion, thus reducing the possibility of postsurgical adhesions. The fabric barrier is preferably in the form of dense fibrous fabric that is added to the scaffold. Preferably, the fibrous fabric is comprised of small diameter fibers that are fused to the top and/or bottom surface of the scaffold. This enables certain surface properties of the structure, such as porosity, permeability, degradation rate and mechanical properties, to be controlled.

The composition, thickness, and porosity of the fibrous layer may be controlled to provide the desired mechanical and biological characteristics. For example, the bioabsorption rate of the fibrous layer may be selected to provide a longer or shorter bioabsorption profile as compared to the underlying scaffold. The fibrous layer may be constructed from the biocompatible polymers discussed above. Additionally, the fibrous layer may provide greater structural integrity to the composite so that mechanical force may be applied to the fibrous side of the structure. In one embodiment the fibrous layer could allow the use of sutures, staples or various fixation devices to hold the composite in place. Preferably the thickness of the fibrous layer is in the range of about 1 micron to 1000 microns.

In another preferred embodiment, the retaining element is constructed from a naturally occurring extracellular matrix material ("ECM"), such as that found in the stomach, bladder, alimentary, respiratory, urinary, integumentary, genital tracts, or liver basement membrane of animals. Preferably, the ECM is derived from the alimentary tract of mammals, such a cow, sheep, dogs, and most preferably from the intestinal tract of pigs. The ECM is preferably, small intestine submucosa ("SIS") which can include the tunica submucosa, along with basilar portions of the tunica mucosa, particularly the lamina muscularis mucosa and the stratum compactum.

For the purposes of this disclosure, it is within the definition of a naturally occurring ECM to clean and/or comminute the ECM, or even to cross-link the collagen fibers within the ECM. However, it is not within the definition of a naturally occurring ECM to extract and purify the natural fibers and reform a matrix material from purified natural fibers. Also, while reference is made to SIS, it is understood that other naturally occurring ECMs are within the scope of this disclosure. Thus, as used herein, the terms "naturally occurring extracellular matrix" or "naturally occurring ECM" are intended to refer to extracellular matrix material that has been cleaned, disinfected, sterilized, and optionally cross-linked.

Where SIS is used, a SIS graft 32 can be harvested in a variety of ways, as will be understood by one skilled in the art. The resulting graft material can have a variety of geometries and consistencies including for example, coiled, helical, spring-like, randomized, branched, sheet-like, tubular, spherical, fragmented, fluidized, comminuted, liquefied, foamed, suspended, gel-like, injectable, powdered, ground, and sheared. In a preferred embodiment, the SIS graft 32 is prepared as a tubular or sheet-like shape which can be used to cover the scaffold of the present invention.

Figure 7:
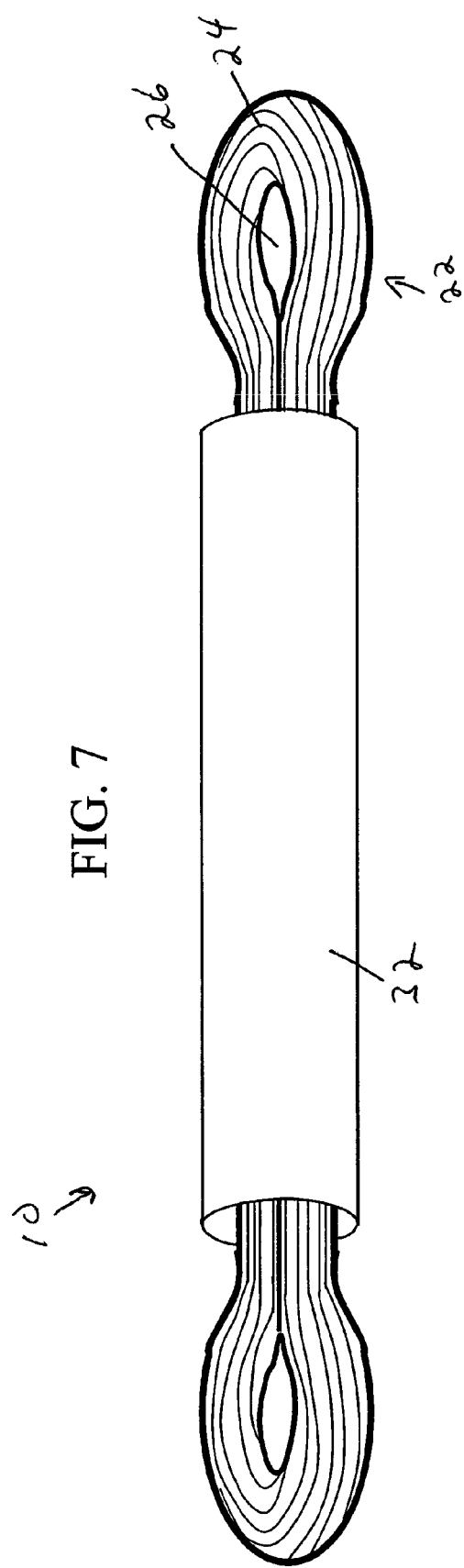

In one embodiment illustrated in FIGS. 6-7, a tubular ECM graft 32 (e.g., SIS) is used as a sleeve to cover at least part of the scaffold. Alternatively, a layer or layers of a sheet-like ECM graft 32 may be wrapped around the exterior of the scaffold.

A ECM graft 32, such as a SIS graft, is particularly advantageous for use with the present invention to provide a smooth exterior surface for easy insertion of the scaffold into a bone tunnel without damaging the longitudinal and/or transverse fibers and to protect minced tissue positioned on the fibers.

The ECM graft 32 can cover at least part of the scaffold and a minced tissue and/or a biological component could be positioned between the ECM graft 32 and the scaffold The minced tissue and/or biological component can be added prior to positioning the ECM graft 32, or the scaffold and ECM graft 32 could be implanted and then the minced tissue and/or biological component could be arthroscopically injected between the ECM graft 32 and the scaffold. In one embodiment, minced ACL tissue and PRP are arthroscopically injected between the ECM graft 32 and the scaffold.

In an alternative embodiment, the ECM may be mixed with the minced tissue or biological component of the present invention, particularly where the ECM is injectable or spreadable. In one embodiment, the ECM is used as a foam mixed with a minced tissue and/or a biological component as discussed above.

In one embodiment of the present invention, the scaffold is used in the treatment of a tissue injury, such as injury to a ligament or tendon. Repairing such injuries involves the steps of obtaining a sample of the damaged living tissue by any of the variety of techniques known to those having skill in the art, processing that sample of living tissue under sterile conditions, such as for example by cutting the tissue, to create at least one minced, finely divided tissue particle, depositing the tissue sample upon the scaffold, such that the tissue sample becomes associated with the scaffold, and placing the scaffold in a desired position relative to the tissue injury. Repairing tissue injuries may also involve placing the scaffold at the site of tissue injury and then depositing the fine tissue particles onto the scaffold. The cells in the tissue particles associated with the scaffold can migrate to the scaffold and begin proliferating and integrating with surrounding tissue at the site of implantation, thereby repairing the tissue injury. This method for repairing tissue injuries can include an additional, optional step. Prior to the step of placing the scaffold in a desired position relative to the tissue injury, the scaffold and associated tissue particles can be incubated for a duration and under conditions effective to allow cells within the tissue particles to migrate from the tissue and begin populating the scaffold The tissue samples used in the present invention are obtained from a donor (autogeneic, allogeneic, or xenogeneic) using appropriate harvesting tools. The tissue samples can be finely minced and divided into small particles either as the tissue is collected, or alternatively, the tissue sample can be minced after it is harvested and collected outside the body. In embodiments, where the tissue sample is minced after it is harvested, the tissue samples can be weighed and then washed three times in phosphate buffered saline. Approximately 300 to 500 mg of tissue can then be minced in the presence of a small quantity, such as, for example, about 1 ml, of a physiological buffering solution, such as, for example, phosphate buffered saline, or a matrix digesting enzyme, such as, for example, 0.2% collagenase in Hams F12. Mincing the tissue divides the tissue into particles or small pieces of approximately 1 mm$^3$. Mincing the tissue can be accomplished by a variety of methods. In one embodiment, the mincing is accomplished with two sterile scalpels using a longitudinal direction, and in another embodiment, the tissue can be minced by a processing tool that automatically divides the tissue into particles of a desired size. In one embodiment, the minced tissue can be separated from the physiological fluid and concentrated using any of a variety of methods known to those having skill in the art, such as for example, sieving, sedimenting or centrifuging. In embodiments where the minced tissue is filtered and concentrated, the suspension of minced tissue preferably retains a small quantity of fluid in the suspension to prevent the tissue from drying out. In another embodiment, the suspension of minced tissue is not concentrated, and the minced tissue can be directly delivered to the site of tissue repair via a high concentration tissue suspension or other carrier such as for example, a hydrogel, fibrin glue, or collagen. In this embodiment, the minced tissue suspension can be covered by any of the biocompatible materials described above to retain the tissue fragments in place.

The minced tissue can then be distributed onto the scaffold using a cell spreader so as to cover the entire scaffold. The minced tissue can also be injected into the scaffold. Optionally, the tissue particles can be adhered to the scaffolds using any of the adhesive agents described above, such as, for example, fibrin glue or platelet rich plasma. In embodiments using fibrin glue or platelet rich plasma, an activator can be used to form a clot or glue. An activator can be, but is not limited to, thrombin, adenosine di-phosphate (ADP), collagen, epinephrine, arachidonic acid, Ristocetin, calcium chloride and combinations thereof. Once the tissue particles and any additional agents have been deposited on the scaffold, the scaffold can then implanted immediately, or alternatively, the scaffold can be cultured in vitro for a duration and under conditions sufficient to allow the cells in the tissue particles to migrate from the tissue particles onto the scaffold. In an embodiment where the tissue repair scaffold is incubated prior to implantation, the scaffold is preferably cultured in vitro for approximately 1-3 weeks in a fibroblast growth medium, such as for example, DMEM-high glucose, supplemented with 20% fetal calf serum (FCS), 100 mg/ml penicillin, 100 mg/ml of streptomycin and 0.25 mg/ml of amphotericin B. In another embodiment, the scaffold may be implanted and then the tissue particles and any addition agents may be deposited onto the scaffold.

The methods of repairing tissue injuries using the tissue scaffolds according to the present invention can be conducted during a surgical operation to repair the tissue injury. Alternatively, the steps of processing the tissue sample to create minced, finely divided tissue particles, depositing the tissue particles upon the scaffold, and/or incubating the scaffold prior to implantation can be conducted at another, sterile location prior to surgical placement of the scaffold relative to the site of injury.

As noted above, the biological component may be added to the scaffold during or after manufacture of the scaffold or before or after the scaffold is installed in a patient. An additional quantity of the biological component may be added after the scaffold is installed. Once access is made into the affected anatomical site (whether by minimally invasive, open or mini-open surgical technique), the scaffold can be affixed to a desired position relative to the tissue injury. Once the scaffold is placed in the desired position, it can be affixed by using a suitable technique. In one aspect, the scaffold can be affixed by a chemical and/or mechanical fastening technique. Suitable chemical fasteners include glues and/or adhesive such as fibrin glue, fibrin clot, and other known biologically compatible adhesives. Suitable mechanical fasteners include sutures, staples, tissue tacks, suture anchors, darts, screws, buttons, pins and arrows. It is understood that combinations of one or more chemical and/or mechanical fasteners can be used. Alternatively, one need not use any chemical and/or mechanical fasteners. Instead, placement of the scaffold can be accomplished through an interference fit of the scaffold with an appropriate site in the tissue to be treated.

In embodiments where the scaffold is used to repair ligament tissue, the scaffold can be used for tissue augmentation, or alternatively, as a stand-alone device. In embodiments where the scaffold is used for augmentation, the scaffold can be used in conjunction with any of a variety of standard, established repair techniques known to those having skill in the art. In embodiments where the scaffold is used for augmentation during ACL repair, surgeons currently use an autograft consisting of ligament tissue, bone-patellar tendons, tendon-bone tendons, hamstring tendons, or iliotibial band to repair tissue, and the scaffold of the present invention can be placed either around the autograft, surrounded by the autograft, or alongside the autograft. In embodiments where the tissue repair element is used as a stand-alone device, the ruptured ligament can be removed and completely replaced by the scaffold, with the ruptured ligament preferably providing source for minced tissue. The scaffold can then be affixed to bone. In the case of ACL repair, one end of the scaffold can be stabilized at the original origin site of the femur, while the other end can be placed at the original insertion site on the tibia.

The following examples are illustrative of the principles and practice of this invention. Numerous additional embodiments within the scope and spirit of the invention will become apparent to those skilled in the art.

Example 1

Figure 9:
FIGS. 8 and 9 are photomicrographs illustrating the results described in Example 1.
Figure 8:
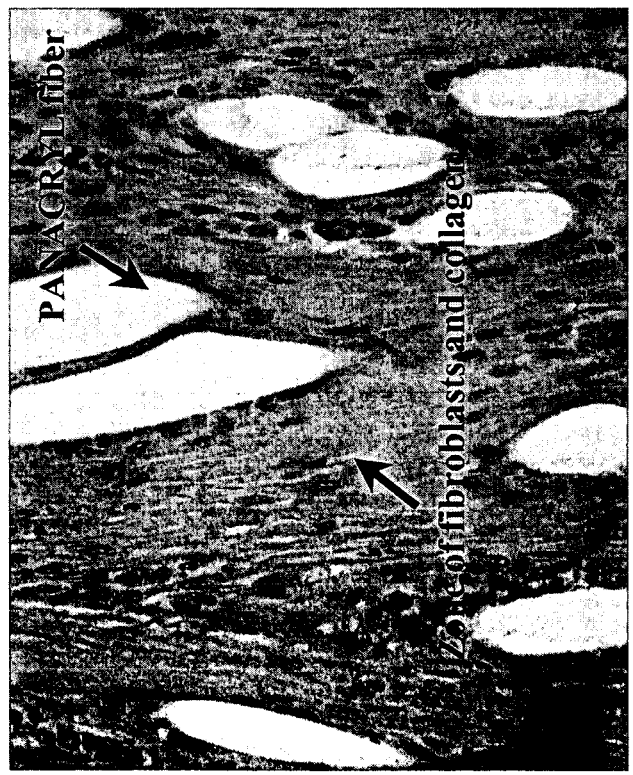

Native anterior cruciate ligament (ACL) tissue was excised from a goat knee and the ACL was reconstructed using a ligament graft resembling that of the type shown in FIG. 4. The graft was formed of PANACRL, a 95:5 copolymer of lactide and glycolide, and was prepared for implantation by incorporating into the graft about 2 ml. of platelet rich plasma (PRP). In one evaluation about 600 mg. minced ACL fragments (about 1 mm. in size) was also incorporated into the graft. The purpose of this study was to evaluate the potential of synthetic scaffolds with autologous growth factors and/or minced tissue to regenerate the ACL. The grafts were 3.5 mm in diameter and the PRP and the minced tissue were placed on the graft before insertion into the tibial and femoral bone tunnels. A VICRYL mesh was sutured around the PANACRYL graft and minced tissue to help retain the tissue on the graft. Fixation of the device was achieved on both the femoral and tibial side using a screw/washer system. After 12 weeks, the ligament portion of the ACL was excised, preserved in 10% buffered formalin fixative, and processed for histology. Histological sections were stained with Hematoxylin and Eosin. FIG. 8 shows the implant that was formed of PANACRYL and PRP only in which newly generated collagen is deposited along the fibers of the scaffold. FIG. 9 shows an image acquired under polarized light of a graft that was formed of PANACRYL, PRP and minced tissue in which new collagen is formed between the fibers and there is order within the new collagen as evidenced by birefringence.

Example 2

A synthetic ACL graft of the type shown in FIG. 4 and formed of PANACRYL, a 95:5 copolymer of lactide and glycolide, was tested mechanically in tension with a gauge length of 8 inches and a strain rate of 1 inch/min. The stiffness was measured to be 160 N/mm and the graft was found to have an ultimate tensile strength of 2600N.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A connective tissue scaffold, comprising:
opposed first and second anchoring eyelets located at opposed ends of the scaffold along a longitudinal axis of the scaffold that extends along a longitudinal length thereof, the eyelets each being formed of a plurality of bioresorbable eyelet region polymeric fibers and defining an open area, and central axes extending through each of the open areas of the first and second anchoring eyelets such that the central axes are disposed substantially perpendicular with respect to the longitudinal axis of the scaffold, each open area being substantially larger than any adjacent void space between the plurality of bioresorbable eyelet region polymeric fibers;
first and second binding regions adjacent to the opposed first and second eyelets, the first and second binding regions being formed of a plurality of bioresorbable first binding region polymeric fibers oriented in a direction substantially parallel to the longitudinal axis of the scaffold and a plurality of bioresorbable second binding region polymeric fibers oriented in a direction that is not substantially parallel to the longitudinal axis, the plurality of first binding region bioresorbable polymeric fibers interlocking with the plurality of bioresorbable second binding region polymeric fibers; and
a central segment, adjoining the first and second binding regions, formed of a plurality of bioresorbable central segment region polymeric fibers oriented in a direction substantially parallel to the longitudinal axis of the scaffold,
wherein an overall fiber density of the central segment is lower than an overall fiber density of the binding regions,
wherein the scaffold further includes a biocompatible, bioresorbable material covering at least a portion of the first and second binding regions and the central segment, and
wherein the bioresorbable material is formed over the first and second anchoring eyelets, the first and second binding regions, and the central segment, and the bioresorbable material is not in a form of a coating.

2. The scaffold of claim 1, wherein the fibers of the first and second binding regions are joined in a weave pattern.

3. The scaffold of claim 1, wherein the bioresorbable material is a biological material.

4. The scaffold of claim 1, further comprising at least one minced tissue particle that is associated with at least a portion of the scaffold, wherein the at least one minced tissue particle includes an effective amount of viable cells that can migrate out of the at least one minced tissue particle and populate the scaffold.

5. The scaffold of claim 4, where in the at least one minced tissue particle comprises a bone-free tissue type selected from the group consisting of tendon, ligament, patellar tendon, anterior cruciate ligament, posterior cruciate ligament, medial collateral ligament, lateral collateral ligament, periosteum, perichondrium, iliotibial band or fascia lata, gracilis tendon, semitendinosis tendon, synovium, skin and combinations thereof.

6. The scaffold of claim 4, wherein the at least one minced tissue particle comprises a bone tissue type that is placed in the first and second binding regions of the scaffold.

7. The scaffold of claim 4, wherein the scaffold further comprises an adhesion agent.

8. The scaffold of claim 7, wherein the adhesion agent comprises an anchoring agent selected from the group consisting of hyaluronic acid, fibrin glue, fibrin clot, collagen gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, synthetic acrylate-based adhesives, platelet rich plasma (PRP), Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

9. The scaffold of claim 7, wherein the adhesion agent comprises a cross-linking agent selected from the group consisting of divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light, pH, temperature, and combinations thereof.

10. The scaffold of claim 4, wherein the scaffold further comprises at least one additional biological component applied thereto.

11. The scaffold of claim 10, wherein the at least one additional biological component comprises heterologous or autologous growth factors, proteins, matrix proteins, peptides, antibodies, antibiotics, anti-inflammatories, chemotactic agents, cell attachment mediators, biologically active ligands, integrin binding sequence, enzymes, cytokines, glycosaminoglycans, viruses, virus particles, nucleic acids, analgesics, cells, platelets, and combinations thereof.

12. The scaffold of claim 1, wherein the bioresorbable polymeric fibers are made from polymers or copolymers formed from monomers selected from the group consisting of lactide, glycolide, dioxanone, and caprolactone.

13. The scaffold of claim 12, wherein the bioresorbable polymeric fibers are made from a copolymer having a ratio of monomers of about 95:5 lactide and glycolide.

14. The scaffold of claim 1, wherein the scaffold is configured for use as a substitute for a ligament graft.

15. The scaffold of claim 14, wherein the scaffold is configured for use as a substitute for a cruciate ligament graft.

16. The scaffold of claim 1, wherein the bioresorbable material is formed over the first and second anchoring eyelets, the first and second binding regions, and the central segment as a wrap, sleeve, or sheath.

17. A connective tissue scaffold, comprising:
opposed first and second anchoring eyelets located at opposed ends of the scaffold along a longitudinal axis of the scaffold that extends along a longitudinal length thereof, the eyelets each being formed of a plurality of bioresorbable eyelet region polymeric fibers and defining an open area, and central axes extending through each of the open areas of the first and second anchoring eyelets such that the central axes are disposed substantially perpendicular with respect to the longitudinal axis of the scaffold, each open area being substantially larger than any adjacent void space between the plurality of bioresorbable eyelet region polymeric fibers;

first and second binding regions adjacent to the opposed first and second eyelets, the first and second binding regions being formed of a plurality of bioresorbable first binding region polymeric fibers oriented in a direction substantially parallel to the longitudinal axis of the scaffold and a plurality of bioresorbable second binding region polymeric fibers oriented in a direction that is not substantially parallel to the longitudinal axis, the plurality of first binding region bioresorbable polymeric fibers interlocking with the plurality of bioresorbable second binding region polymeric fibers; and a central segment, adjoining the first and second binding regions, formed of a plurality of bioresorbable central segment region polymeric fibers oriented in a direction substantially parallel to the longitudinal axis of the scaffold, wherein an overall fiber density of the central segment is lower than an overall fiber density of the binding regions; and wherein the scaffold further includes a biocompatible, bioresorbable material covering at least a portion of the first and second binding regions and the central segment, wherein the bioresorbable material is a biological material, wherein the bioresorbable material is small intestine submucosa, and wherein the bioresorbable material is formed over the first and second anchoring eyelets, the first and second binding regions, and the central segment, and the bioresorbable material is not in a form of a coating.

18. The scaffold of claim 17, wherein the fibers of the first and second binding regions are joined in a weave pattern.

19. The scaffold of claim 17, further comprising at least one minced tissue particle that is associated with at least a portion of the scaffold, wherein the at least one minced tissue particle includes an effective amount of viable cells that can migrate out of the at least one minced tissue particle and populate the scaffold.

* * * * *